(12) United States Patent
Briggs et al.

(10) Patent No.: US 6,486,302 B1
(45) Date of Patent: Nov. 26, 2002

(54) HM2 CDNA AND RELATED POLYPEPTIDE

(75) Inventors: Steven P. Briggs, DelMar, CA (US); Gurmukh Johal, Columbia, MO (US); Dilbag Singh Multani, Columbia, MO (US)

(73) Assignee: Pioneer Hi-Bred International, Inc., Des Moines, IA (US)

( * ) Notice: Subject to any disclaimer, the term of this patent is extended or adjusted under 35 U.S.C. 154(b) by 16 days.

(21) Appl. No.: 09/768,585

(22) Filed: Jan. 24, 2001

Related U.S. Application Data

(62) Division of application No. 09/231,227, filed on Jan. 14, 1999, now Pat. No. 6,211,440.
(60) Provisional application No. 60/071,684, filed on Jan. 16, 1998.

(51) Int. Cl.$^7$ .......................... A61K 35/80; A01H 1/00; C07H 21/04

(52) U.S. Cl. ...................... 530/376; 930/230; 800/278; 800/279; 536/23.6

(58) Field of Search .......................... 536/23.6; 435/419, 435/424; 800/278, 279, 298, 301; 530/376; 514/12; 930/230

(56) References Cited

U.S. PATENT DOCUMENTS 5,589,611 A 12/1996 Briggs et al.

FOREIGN PATENT DOCUMENTS

WO WO 97/23627 7/1997

OTHER PUBLICATIONS

Han et al., "Cloning and Mapping of a putative barley NADPH–dependent HC–Toxin Reductase", MPMI, 10(2), 234–239, 1997.*
Han et al., Database: PIR_68, Accession NO: T06197, Apr. 30, 1999, "HC–toxin reductase" alignment of amino acid sequence of SEQ ID NO: 2.*
Multani, et al., 1998, *Proc. Natl. Acad. Sci. USA*, 95: 1686–1691, "Plant–pathogen microevolution: Molecular basis for the origin of a fungal disease in maize".
Scheffer, et al., 1965, *Phytopathology* 55, 1037–1038, "Host–Specific Metabolite from *Helminthosporium carbonum*".
Scheffer, et al., 1967, *Phytopathology* 57, 1288–1289, "Inheritance of Toxin Production and Pathogenicity in*Cochliobolus carbonum*and*Cochliobolus victoria*".
Gross, M.L., et al., 1982, *Tetrahedron Lett.* 23, 5381–5384, "The Structure of the Toxin from *Helminthosporium Carbonum*".
Walton, J.D., et al., 1982, *Biochem. Biophys. Res. Commun.* 107, 785–794, "Purification and Structure of the Host–Specific Toxin from *Helminthosporium Carbonum* Race 1".
Comstock, J.C., et al., 1973, *Phytopathology* 63, 24–29, "Role of Host–Selective Toxin in Colonization of Corn Leaves by *Helminthosporium carbonum*".
Panaccione, D.C., et al., 1992, *Proc. Natl. Acad. Sci*, USA 39, 6590–6594, "A cyclic peptide synthetase gene required for pathogenicity of the fungus *Cochliobolus carbonum* on maize".
Scott–Craig, J.S., et al., 1992, *J. Biol. Chem.* 267, 26044–26049, "The Cyclic Peptide Synthetase Catalyzing HC–toxin Production in the Filamentous Fungus *Cochliobolus carbonum*Is Encoded by a 15.7–Kilobase Open Reading Frame".
Brosch, et al., 1995, *Plant Cell* 7: 1941–1950, "Inhibition of Maize Histone Deacetylases by HC Toxin, the Host–Selective Toxin of Cochliobolus carbonum".
Ullstrup, A.J., 1941, *J. Agric. Res.* 63, 331–334.
Meeley, R.B., et al., Nester and Verma (eds.), *Advances in Molecular Genetics of Plant–Microbe Interactions*, 463–467, "Molecular Biology and Biochemistry of Hm1, a Maize Gene for Fungal Resistance".
Nelson, O.E., et al., 1964, *J. Hered.* 55, 195–199, "Resistance to Leaf Spot in Maize".
Johal, et al., 1992, *Science* 258, 985–987, "Reductase Activity Encoded by the HM1 Disease Resistance Gene in Maize".
Meeley, R.B., et al., 1992, *Plant Cell* 4, 71–77, "A Biochemical Phenotype for a Disease Resistance Gene of Maize".
Walton, J.D., Kleinkauf and Dohren (eds.)., *Walter de Gruyter Berlin*, New York, 1990, 179–203, "Biochemistry of Peptide Antibiotics".
Darkan–Rattray, et al., 1996, *Proc. Natl. Acad. Sci. USA* 93:13143–13147, "Apicidin: A novel antiprotozoal agent that inhibits parasite histone deacetylase".
Kim, et al., 1987, *Physiol Mol. Plant Pathol*, 30, 433–440, "Essentiality of the ketone function for toxicity of the host–selective toxin produced by *Helminthosporium carbonum*".
Barron, et al., A.H.S., 1966, *Can. J. Bot.* 44: 861–869, "Verticillium Chlamydosporium and Its Relationships to Diheterospora, Stemphyliopsis, and Paecilomyces".

(List continued on next page.)

*Primary Examiner*—Karen Cochrane Carlson
*Assistant Examiner*—Rita Mitra
(74) *Attorney, Agent, or Firm*—Pioneer Hi-Bred International, Inc.

(57) ABSTRACT

The invention provides isolated Hm2 nucleic acids, and their encoded proteins. The present invention provides methods and compositions relating to altering Hm2 concentration and/or composition of plants. The invention further provides expression cassettes, host cells, transgenic plants, and antibody compositions. Also, the invention provides methods of identifying plant transformation by survival of transformed plant cells or tissues on a cyclic tetrapeptide toxin. The invention further provides methods of imparting disease resistance to plants susceptible to fungal pathogens, which utilize cyclic tetrapeptide toxins.

14 Claims, No Drawings-

OTHER PUBLICATIONS

Hirota, et al., 1973, *Agric. Biol. Chem.* 37: 955–956, "Structure of Cyl–2, a Novel Cyclotetrapeptide from *Cylindrocladium scoparium*".

Yoshida, et al., 1992, *Jpn J Cancer Res* 83: 324–328, "A Novel Tetracyclic Peptide, Trapoxin, Induces Phenotypic Change from Transformed to Normal in sis–Oncogene–transformed NIH3T3 Cells".

Kijima et al., 1993, *J. Biol. Chem.*, 268: 22429–22435,, "Trapoxin, an Antitumor Cyclic Tetrapeptide, Is an Irreversible Inhibitor of mammalian Histone Deacetylase".

Umehara, et al., 1983, *J. Antibiot.* 36: 478–483, "Studies on WF–3161, a New Antitumor Antibiotic".

Meeley, et al., 1991, *Plant Physiol.* 97, 1080–1086, "Enzymatic Detoxification of HC–toxin, the Host–Selective Cyclic Peptide from *Cochliobolus carbonum*".

Walton, 1991, *Mycol–Ser.*, 8: 225–249, "Genetics and Biochemistry of Toxin Synthesis in *Cochliobolus* (*Helminthosporium*)".

Walton, et al., 1983, *Physiological Plant Pathology*, 22, 371–376, "The epoxide in HC–toxin is required for activity against susceptible maize".

Fushimi, et al., 1996, *Derwent Publications Section Ch, Week 9620*, "Rice NADH–dependent reductase gene—used in breeding technology to provide resistance to plant pathogenic microbes".

Nissan Chem Ind. Ltd., 1996, *Geneseq Accession No. T13486*, "Rice NADH–dependent reductase gene".

Walton, et al., 1985, *Experientia*, 41: 348–350, "Reciprocal biological activities of the cyclic tetrapeptides chlamydocin and HC–toxin".

* cited by examiner

SEQUENCE LISTING

```
<160> NUMBER OF SEQ ID NOS: 7

<210> SEQ ID NO 1
<211> LENGTH: 1271
<212> TYPE: DNA
<213> ORGANISM: Zea mays
<220> FEATURE:
<221> NAME/KEY: CDS
<222> LOCATION: (20)...(1100)

<400> SEQUENCE: 1
gggagaagag ctagagggg atg ggt ggc ggc acg gtg gtg tgt gtc acc ggc      52
                    Met Gly Gly Gly Thr Val Val Cys Val Thr Gly
                     1               5                  10 ggc agc ggc tac ctc ggg agc tgg ctc gtc agg aag ctc ctc ggc aga      100
Gly Ser Gly Tyr Leu Gly Ser Trp Leu Val Arg Lys Leu Leu Gly Arg
             15                  20                  25 ggc tgc gtc gtc cac gcc acc ctg cgg agc ctc gcg gac gag aag aag      148
Gly Cys Val Val His Ala Thr Leu Arg Ser Leu Ala Asp Glu Lys Lys
         30                  35                  40 acg ggg ctg ctc cgg gcg ctc ccc ggc gcg gcg gag cgg ctg cgg ctg      196
Thr Gly Leu Leu Arg Ala Leu Pro Gly Ala Ala Glu Arg Leu Arg Leu
     45                  50                  55 ttc gag gcg gac atg tac gac gcc gac acc ttc gag ccc gcc atc gcc      244
Phe Glu Ala Asp Met Tyr Asp Ala Asp Thr Phe Glu Pro Ala Ile Ala
 60                  65                  70                  75 ggc tgc cac ttc gtc ttc ctc gtc gcc acg ccc ctg acg cac gac ccc      292
Gly Cys His Phe Val Phe Leu Val Ala Thr Pro Leu Thr His Asp Pro
                 80                  85                  90 acc agc acc aag tac aag aac acg acg gag gcg gcg gtg gac gcg gcg      340
Thr Ser Thr Lys Tyr Lys Asn Thr Thr Glu Ala Ala Val Asp Ala Ala
             95                 100                 105 cgc atc atc ctc cgg cag tgc gcg ctg tcc ggc acg gtg aag cgc gtc      388
Arg Ile Ile Leu Arg Gln Cys Ala Leu Ser Gly Thr Val Lys Arg Val
         110                 115                 120 atc cac acg gcc tcg gtc acg gcc gcg tcg ccg ctc aag gag gac ggc      436
Ile His Thr Ala Ser Val Thr Ala Ala Ser Pro Leu Lys Glu Asp Gly
     125                 130                 135 agc ggg tac aag gac ttc gcc gac gag tcc aat tgg acg ccg ctc aac      484
Ser Gly Tyr Lys Asp Phe Ala Asp Glu Ser Asn Trp Thr Pro Leu Asn
140                 145                 150                 155 ctc tcc tgc gaa ttc agc aac gct tac ctg gac gac tac gtg cgg tcc      532
Leu Ser Cys Glu Phe Ser Asn Ala Tyr Leu Asp Asp Tyr Val Arg Ser
                 160                 165                 170
```

```
aag acg ctg tcg gag aag gag cta ctg agc tac tcc tcc tcc tcc tcc    580
Lys Thr Leu Ser Glu Lys Glu Leu Leu Ser Tyr Ser Ser Ser Ser Ser
            175                 180                 185 tcc aag gaa gac gac cgg acc cgg gcg ttg gag gtg gtc acc cta acg    628
Ser Lys Glu Asp Asp Arg Thr Arg Ala Leu Glu Val Val Thr Leu Thr
        190                 195                 200 tgc ggg ctc gtc ggc ggc gac agc atc cag acg tac ctg tgg ggc aac    676
Cys Gly Leu Val Gly Gly Asp Ser Ile Gln Thr Tyr Leu Trp Gly Asn
        205                 210                 215 atc gcc gcg att ctg gcg ccg ctg acg ggg caa gcg gtc aat cac aac    724
Ile Ala Ala Ile Leu Ala Pro Leu Thr Gly Gln Ala Val Asn His Asn
220                 225                 230                 235 gcc ctc ctc ttc ttg caa gcg ctg ctg ggc tcc gtc ccg ctg gtg cac    772
Ala Leu Leu Phe Leu Gln Ala Leu Leu Gly Ser Val Pro Leu Val His
                240                 245                 250 gtt gag gac gtc tgc cag gca cac gtc ttc tgc atg gag cag gag tcc    820
Val Glu Asp Val Cys Gln Ala His Val Phe Cys Met Glu Gln Glu Ser
            255                 260                 265 atg acc ggc cgc ttc ctc tgc gcc gcc ggg tac ccc aac atg cgt gac    868
Met Thr Gly Arg Phe Leu Cys Ala Ala Gly Tyr Pro Asn Met Arg Asp
        270                 275                 280 atc gtc gac cac ttt gcc gca aag caa ccc cga cct caa gat aca gct    916
Ile Val Asp His Phe Ala Ala Lys Gln Pro Arg Pro Gln Asp Thr Ala
    285                 290                 295 gac tca agt gac cgg aga agg ggt cag gat tca gcc caa cac cag caa    964
Asp Ser Ser Asp Arg Arg Arg Gly Gln Asp Ser Ala Gln His Gln Gln
300                 305                 310                 315 gct gga gga ctt ggg gtt cag att caa gta tgg agt gga gga gac gct    1012
Ala Gly Gly Leu Gly Val Gln Ile Gln Val Trp Ser Gly Gly Asp Ala
                320                 325                 330 gga ctg cag cgt cga gtg cgc caa gag gct ggg aga gct cta gat gca    1060
Gly Leu Gln Arg Arg Val Arg Gln Glu Ala Gly Arg Ala Leu Asp Ala
            335                 340                 345 tgc tac gca tgc atg cgc agc att ggg att cag cga ctg t gatacgagta  1110
Cys Tyr Ala Cys Met Arg Ser Ile Gly Ile Gln Arg Leu
        350                 355                 360 agtatggtgg tatactggta tcatgttaat acgtgcgtat attgggtcga ttcatcccac  1170
cagagtttga actgttccgt attcccatct gtttcccgtg atcataaaat aaaaacagta  1230
aaataaaaaa aaaaaaaaaa agtactagtc gacgcgtggc c                      1271
```

<210> SEQ ID NO 2
<211> LENGTH: 360
<212> TYPE: PRT
<213> ORGANISM: Zea mays

<400> SEQUENCE: 2

```
Met Gly Gly Gly Thr Val Val Cys Val Thr Gly Ser Gly Tyr Leu
 1               5                  10                  15

Gly Ser Trp Leu Val Arg Lys Leu Leu Gly Arg Gly Cys Val Val His
                20                  25                  30

Ala Thr Leu Arg Ser Leu Ala Asp Glu Lys Lys Thr Gly Leu Leu Arg
            35                  40                  45

Ala Leu Pro Gly Ala Ala Glu Arg Leu Arg Leu Phe Glu Ala Asp Met
        50                  55                  60

Tyr Asp Ala Asp Thr Phe Glu Pro Ala Ile Ala Gly Cys His Phe Val
65                  70                  75                  80

Phe Leu Val Ala Thr Pro Leu Thr His Asp Pro Thr Ser Thr Lys Tyr
```

```
                    85                  90                  95
Lys Asn Thr Thr Glu Ala Ala Val Asp Ala Ala Arg Ile Ile Leu Arg
                100                 105                 110
Gln Cys Ala Leu Ser Gly Thr Val Lys Arg Val Ile His Thr Ala Ser
            115                 120                 125
Val Thr Ala Ala Ser Pro Leu Lys Glu Asp Gly Ser Gly Tyr Lys Asp
        130                 135                 140
Phe Ala Asp Glu Ser Asn Trp Thr Pro Leu Asn Leu Ser Cys Glu Phe
145                 150                 155                 160
Ser Asn Ala Tyr Leu Asp Asp Tyr Val Arg Ser Lys Thr Leu Ser Glu
                165                 170                 175
Lys Glu Leu Leu Ser Tyr Ser Ser Ser Ser Ser Lys Glu Asp Asp
            180                 185                 190
Arg Thr Arg Ala Leu Glu Val Val Thr Leu Thr Cys Gly Leu Val Gly
        195                 200                 205
Gly Asp Ser Ile Gln Thr Tyr Leu Trp Gly Asn Ile Ala Ala Ile Leu
    210                 215                 220
Ala Pro Leu Thr Gly Gln Ala Val Asn His Asn Ala Leu Leu Phe Leu
225                 230                 235                 240
Gln Ala Leu Leu Gly Ser Val Pro Leu Val His Val Glu Asp Val Cys
                245                 250                 255
Gln Ala His Val Phe Cys Met Glu Gln Glu Ser Met Thr Gly Arg Phe
            260                 265                 270
Leu Cys Ala Ala Gly Tyr Pro Asn Met Arg Asp Ile Val Asp His Phe
        275                 280                 285
Ala Ala Lys Gln Pro Arg Pro Gln Asp Thr Ala Asp Ser Ser Asp Arg
    290                 295                 300
Arg Arg Gly Gln Asp Ser Ala Gln His Gln Gln Ala Gly Gly Leu Gly
305                 310                 315                 320
Val Gln Ile Gln Val Trp Ser Gly Gly Asp Ala Gly Leu Gln Arg Arg
                325                 330                 335
Val Arg Gln Glu Ala Gly Arg Ala Leu Asp Ala Cys Tyr Ala Cys Met
            340                 345                 350
Arg Ser Ile Gly Ile Gln Arg Leu
        355                 360

<210> SEQ ID NO 3
<211> LENGTH: 3352
<212> TYPE: DNA
<213> ORGANISM: Zea mays

<400> SEQUENCE: 3
cattgatgca taaattacct atgcttttc aactacaacc ctcagcctgt tattttatgc      60
atgatatgat tttgagacaa gtttttatgg ccacccagcc gcttgccgca atcaatccct    120
gatatatttg ttacaaatga tttaagaaaa ggtgtgagtt ttcaaaagaa aatgcttttc    180
aaaatgtgta tgatgaaggg ttttcaccct tatcaccttt gagtagggat gatcagggac    240
tccctggttt aggggagggc ctaaggtgat ggctcagctg gtttaggtgt gagcagaagg    300
attgtcccct cacataagga ccggtttgtc atcctttact acctgtactc atgataagta    360
caaccactcg agactgtgtg gcagtcact caatctgaac tcgtacggtc caaccccagg     420
ttatgaaggc tggggagcac cggaggata aggaagggga atgttttgtc cggtttggac      480
atggcggtgg cctgattcct tccgtataac cgttaaggtt agaacgtgcg aggaaagaaa    540
```

```
atattcggca ttcggttctc acgacgtgag atcgcagaaa ccggattagt gggtaaagtg      600
tacatttttg cgcagagttt gaaaacctat ttgaatagtc tgtgtccaca ggaatggacg      660
agtctggtat ggtatgacaa ttaatgtttt gttttaaaaa aggtgcgtt tgagaaaagt       720 ggtttttaaa aggtccggcg gttgagccgt gagctatggt ggacgagaag tccagaagct      780 gttttttgaaa atgaaaacca gtgggaaact gctgagatac ctggatggtt tagtccaagg    840
gattttgttt tatattgaaa aacttcctgc tcctttggga gaggatgcgc tttgcaaaat     900
acaaaatgtt tttcaaaaca accctgcata aatattgct gtttctgcaa aatatcctga      960
gctccacata ttccatgcat tatatctgat ttccccattc cgcgggtgaa ggtgggctgc    1020
taagtacgtt tgtactcacc cttgcttatt tgttgttttt cagaaaaagg gatcgggta    1080 agagttacat ctaaattaaa accctggctt cgcctctgct cacagtttat gccaaaattg    1140
ctgataaagt ggcacttcag attatccgag aagttaatgg tgtagaaatt agaaacgaag    1200
taacttatat tctctaggtc tcgcgcatcg cctagtgccc tagtccatcg agtagcaacg    1260
aagcttgaca gcaacggaga agaccatgaa cagcagtagc agtgaagtgc aggtgtgcgt    1320
caccggtggc gccgggttca tcggctccta cctcgtcaag aagctcctcg agaagggcta    1380
caccgtccac gccacgctgc ggaacaccgg tgcgcgctgc gcgagccccc tcttccttcc    1440
atagcttcgg tcgtcgtcgc tcactctgat gatcggattc atttgatgac cgcgcgcaga    1500
ggacgaggag aagaccgggc tgctgcggcg gctggtcccc ggcgcggcgg agcgtctgcg    1560
gttgttccgt tgttcgaggc cgacctcttc gacgccgcca ccttcgcgcc ggcgatcgct    1620
gggtgccagt tcgtcttcct cgtcgccacg ccatacgggc tcgaagccgc cggatccaag    1680
gtaccaacca catcgcactt tcgtcccttg tcttccacag aaaacttatt ttgactggat    1740
cagcgaagaa accataggat cttaagcgcg cacacaaaaa caattccaag gtcatttgat    1800
tgagctcgat tctattgcgt tgtcgcgcct tgaaacgaaa ttctattcta tcgcctggca    1860
gtacaagagc acggcggaag ctgcagtggc cgcggtgcgc gtgatcctcc ggcagtgcga    1920
ggagtccaag acggtgaagc gcgtcatcca caccgcctcc atatcgaccg cttcgccgct    1980
caaggacaag gaagcggagg gttccggcga tgggtacaaa tatttcatca gcgaatcgtg    2040
ttggacgccg ctcaacgttg actaccacct tcgcagcgca cacttcgacg tgagcaactg    2100
tgtgctctgc tagtgctgac cgagtctgct gctgatgatt tatttaactt tttagctaat    2160
ccttctttta gcggaaaatg cgatttaatt aaacgggcaa aagcgacaaa ccgtttgcag    2220
aagtacatac tggcaaagct gcggtcggag caggagctcc tgagctacaa cggcggcgag    2280
agcccggcgt tcgaagtggt gacctgcccc tggggctcgt cgcgggagac acggtcctcg    2340
gccacgcgcc ggagacgctg gagcacgccg tgtcgccggt gtcacgggaa gagctctcct    2400
tcaagttcct ccgctgctg cagagcttgc tcggctccga gccgctggtg cacgtcgacg    2460
acgcctgcga ggcgctcctc ttctgcatgg agcgcccgtc catcgccggc cgcttcttct    2520
gcgccgccgc gtacccgagc atccacgaca tcacggacca ctacgccagc aagttccctc    2580
acctcgacgt cctcagagcg taaatccttt tacaccatga gctaccatgc ttctaagaag    2640
ggaacagcat gccatgcaca catacacatt tatttatttg tcctctattc tcgattatct    2700
ttaggcctta ttcgtttgtg tcagattgtt cgtttggtgt cagattgcac ccgaaatcgt    2760
tatagctaat caaagtttat ataaattaga gaaacaatcc gattaagaat cggtccgatt    2820
accaatcgtc cttaacaacc gaacgcgctt tattcttatc ttttttagaa aagcatagta    2880
acgtttatgc agttcacaaa aacaagggtg gcaaaccagc tatccaaaca catcgaaaca    2940
```

-continued

```
aaatgggaca caatcacaca acaccaaacc ctccacgcat ctaacatcta aaaacacgac    3000
cacaccagca acacaaaagg aaagctgcta ccaaagcaag ctctatactc tacatccaag    3060
tcctgtgtgt gtttccaaaa gttctccagc catgtcttca taatcttggc atctccctcc    3120
ttcagtagta agctccatat ctacaagaac acaaacattt ttttttttct tttgaaaaac    3180
ttcgctcgac aactttggat tttttccccg acgcccatct tatttcaaat attccaagta    3240
ccctataaaa ttacagagaa catgaaaagt ttagtactcc tatgacaatc ctttcaacca    3300
agcagaacca cttaatggtt cgtcaagaaa tttaatcccc tcaaatcatc tt            3352
```

<210> SEQ ID NO 4
<211> LENGTH: 301
<212> TYPE: PRT
<213> ORGANISM: Zea mays

<400> SEQUENCE: 4

```
Met Asn Ser Ser Ser Glu Val Gln Val Cys Val Thr Gly Gly Ala
  1               5                  10                  15

Gly Phe Ile Gly Ser Tyr Leu Val Lys Lys Leu Leu Glu Lys Gly Tyr
             20                  25                  30

Thr Val His Ala Thr Leu Arg Asn Thr Gly Glu Asp Arg Ala Ala Ala
         35                  40                  45

Ala Ala Gly Pro Arg Gly Gly Ala Ser Ala Val Val Pro Leu Phe
     50                  55                  60

Glu Ala Asp Leu Phe Asp Ala Ala Thr Phe Ala Pro Ala Ile Ala Gly
 65                  70                  75                  80

Cys Gln Phe Val Phe Leu Val Ala Thr Pro Tyr Gly Leu Glu Ala Ala
                 85                  90                  95

Gly Ser Lys Tyr Lys Ser Thr Ala Glu Ala Ala Val Ala Ala Val Arg
            100                 105                 110

Val Ile Leu Arg Gln Cys Glu Glu Ser Lys Thr Val Lys Arg Val Ile
        115                 120                 125

His Thr Ala Ser Ile Ser Thr Ala Ser Pro Leu Lys Asp Lys Glu Ala
    130                 135                 140

Glu Gly Ser Gly Asp Gly Tyr Lys Tyr Phe Ile Ser Glu Ser Cys Trp
145                 150                 155                 160

Thr Pro Leu Asn Val Asp Tyr His Leu Arg Ser Ala His Phe Asp Lys
                165                 170                 175

Tyr Ile Leu Ala Lys Leu Arg Ser Glu Gln Glu Leu Leu Ser Tyr Asn
            180                 185                 190

Gly Gly Glu Ser Pro Ala Phe Glu Val Val Thr Cys Pro Trp Gly Ser
        195                 200                 205

Ser Arg Glu Thr Arg Ser Ser Ala Thr Arg Arg Arg Trp Ser Thr
    210                 215                 220

Pro Cys Arg Arg Cys His Gly Lys Ser Ser Pro Ser Ser Ser Gly
225                 230                 235                 240

Cys Cys Arg Ala Cys Ser Ala Pro Ser Arg Trp Cys Thr Ser Thr Thr
                245                 250                 255

Pro Ala Arg Arg Ser Ser Ala Trp Ser Ala Arg Pro Ser Pro Ala
            260                 265                 270

Ala Ser Ser Ala Pro Pro Arg Thr Arg Ala Ser Thr Thr Ser Arg Thr
        275                 280                 285

Thr Thr Pro Ala Ser Ser Leu Thr Ser Thr Ser Ser Glu
    290                 295                 300
```

```
<210> SEQ ID NO 5
<211> LENGTH: 26
<212> TYPE: DNA
<213> ORGANISM: Zea mays

<400> SEQUENCE: 5
tcggctcctg gctcgtcagg aagctc                                              26

<210> SEQ ID NO 6
<211> LENGTH: 21
<212> TYPE: DNA
<213> ORGANISM: Zea mays

<400> SEQUENCE: 6
ggaaggggag aagagctaga g                                                   21

<210> SEQ ID NO 7
<211> LENGTH: 21
<212> TYPE: DNA
<213> ORGANISM: Zea mays

<400> SEQUENCE: 7
tccgcctcga acagccgcag c                                                   21
```

HM2 CDNA AND RELATED POLYPEPTIDE

CROSS REFERENCE RELATED TO APPLICATION

This application claims the benefit of U.S. Provisional Application No. 60/071,64 filed Jan. 16, 1998 and is a Divisional of U.S. application Ser. No. 09/231,227 filed Jan. 14, 1999, now U.S. Pat. No. 6,211,440 and are hereby incorporated by reference.

TECHNICAL FIELD

The present invention relates generally to plant molecular biology. More specifically, it relates to nucleic acids and methods for modulating their expression in plants.

BACKGROUND OF THE INVENTION

Disease resistance genes are defined as Mendelian factors that cosegregate with the resistance trait. The genes Hm1 and Hm2 control resistance to *Cochliobolus carbonum* Nelson race 1 and are among the first disease resistance genes to be described. The disease caused by *C. carbonum* race 1 can be devastating, resulting in yield losses of 80% or more due to plant death and grain mold. In 1938, this disease was first reported in Indiana on an inbred line, Pr (Ullstrup, A. J. (1941) *Phytopathology* 31, 508–521, which was bred in Iowa from an open-pollinated cultivar, Proudfit Reid (Gerdes, J. T., Behr, C. F., Coors, J. O. & Tracy, W. F. (1993) Compilation of North American Maize Breeding Germplasm (Am. Soc. Agron., Madison, Wis.)). Disease symptoms included grayish tan necrotic spots with concentric rings on the foliage, and infection often resulted in severe molding of the ears and premature killing of the plant. Hm1 and Hm2 are the only disease resistance genes that are known to be fixed at a high frequency in maize germplasm.

Genetic studies revealed that pathogenicity of *C. carbonum* race 1 is determined by a single locus, Tox2 which also confers the ability to produce HC toxin (Scheffer, R. P. & Ullstrup, A. J. (1965) *Phytopathology* 55, 1037–1038; Scheffer, R. P., et al., (1967) *Phytopathology* 57, 1288–1289). HC toxin is a cyclic tetrapeptide of the structure cyclo (D-prolyl-L-alanyl-D-alanyl-L-Aeo), where the unusual amino acid Aeo stands for 2-amino-9,10-epoxy-8-oxodecanoic acid (Gross, M. L, et al., (1982) *Tetrahedron Lett.* 23, 5381–5384, Walton, J. D., et al., (1982) *Biochem. Biophys. Res. Commun.* 107, 785–794), and appears to be the sole determinant of pathogenicity. Genetic variants that do not produce HC toxin are unable to colonize much beyond the site of penetration and, therefore, cause only chlorotic or necrotic flecks on leaves (Comstock, J. C. & Scheffer, R. P. (1973) Phytopathology 63, 24–29, Panaccione, D. C., et al., (1992) *Proc. Natl. Acad. Sci. USA* 39, 6590–6594). The Tox2 locus has been cloned and found to encode the enzymes required for the biosynthesis of HC toxin (Panaccione, et al. supra; Scott-Craig, J. S., et al., (1992) *J. Biol Chem.* 267, 26044–26049). It is not clear how HC toxin allows colonization of susceptible maize. However, by virtue of its inhibitory action on histone deacetylases, HC toxin may interfere with the induction of defense genes in maize, thereby leaving the plant vulnerable to colonization by the pathogen (Brosch, et al., *Plant Cell* 7:1941–1950 (1995)).

*C. carbonum* race 1 is one of the most aggressive pathogens of maize. Fortunately, most maize germplasm is resistant. The dominant gene, Hm1 confers complete protection (Ullstrup, A. J. (1941) *J. Agric. Res.* 63, 331–334; Meeley, R. B., et al., *Advances in Molecular Genetics of Plant-Microbe Interactions*, 463–467, Nester and Verma (eds.) Kluwer Academic Publishers, Netherlands), and it maps to the long arm of chromosome 1 (1L). Another gene, Hm2, provides partial, adult plant resistance, and it maps to 9L (Nelson, O. E. & Ulistrup, A. J. (1964) *J. Hered.* 55, 195–199). The cloning of the Hm1 gene has revealed that, by encoding HC toxin reductase (HCTR), Hm1 inactivates HC toxin, and this result is sufficient to prevent infection (Johal, G. S. & Briggs, S. P. (1992) *Science* 258, 985–987; Meeley, R. B., et al., (1992) *Plant Cell* 4, 71–77; Briggs, et al., U.S. Pat. No. 5,589,611. The foregoing references are herein incorporated by reference.).

In the present invention the Hm2 polynucleotide sequence has been cloned and sequenced. The Hm2 polynucleotide functions to inactivate HC toxin and other cyclic tetrapeptides such as cyl-2, chlamydocin, apicidin and WF-3161 (Walton, J. D., *Biochemistry of Peptide Antibiotics*, 179–203, Kleinkauf and Dohren (eds.), Walter de Gruyter Berlin, New York (1990); Darkan-Rattray et al, *Proc. Natl. Acad. Sci. USA* 93:13143–13147 (1996). The foregoing references are herein incorporated by reference.). Therefore, the Hm2 polynucleotide can be used to prevent fungal infection in plants or as a selectable marker gene in plant transformation.

SUMMARY OF THE INVENTION

Generally, it is the object of the present invention to provide nucleic acids and proteins relating to Hm2. It is an object of the present invention to provide transgenic plants comprising the nucleic acids of the present invention and methods for modulating, in a transgenic plant, the expression of the nucleic acids of the present invention.

Therefore, in one aspect, the present invention relates to an isolated nucleic acid comprising a member selected from the group consisting of (a) a polynucleotide having a specified sequence identity to a polynucleotide encoding a polypeptide of the present invention; (b) a polynucleotide which is complementary to the polynucleotide of (a); and, (c) a polynucleotide comprising a specified number of contiguous nucleotides from a polynucleotide of (a) or (b). The isolated nucleic acid can be DNA.

In another aspect, the present invention relates to expression cassettes, comprising a nucleic acid of the present invention operably linked to a promoter or expression cassettes containing the promoter of the present invention operably linked to a heterologous gene.

In another aspect, the present invention is directed to a host cell into which has been introduced the expression cassette.

In a further aspect, the present invention relates to an isolated protein comprising a polypeptide having a specified number of contiguous amino acids encoded by an isolated nucleic acid of the present invention.

In another aspect, the present invention relates to an isolated nucleic acid comprising a polynucleotide of specified length, which selectively hybridizes under stringent conditions to a polynucleotide of the present invention, or a complement thereof. In some embodiments, the isolated nucleic acid is operably linked to a promoter.

In another aspect, the present invention relates to an expression cassette comprising a nucleic acid amplified from a library as referred to supra, wherein the nucleic acid is operably linked to a promoter. In some embodiments, the present invention relates to a host cell transfected with this expression cassette. In some embodiments, the present invention relates to a protein of the present invention which is produced from this host cell.

In yet another aspect, the present invention relates to a transgenic plant comprising an expression cassette comprising a plant promoter operably linked to any of the isolated nucleic acids of the present invention. The present invention also provides transgenic seed from the transgenic plant.

Additionally, the Hm2 polynucleotides can be inserted using conventional transformation methods into the genomes of plants, which lack the gene and are susceptible to disease caused by fungal pathogens utilizing HC toxin or other cyclic tetrapeptide toxins. Resulting transformants are resistant to the disease.

Further, the Hm2 polynucleotide can be used in conjunction with the HC-toxin or other cyclic tetrapeptide toxins in a selectable marker system for use in plant transformation. When the cloned Hm2 polynucleotide is linked to appropriate regulatory sequences for expression in plant cells and cotransformed into plant cells along with another quantitative or qualitative trait which is not selectable, it confers upon transformants a resistance to HC toxin or other cyclic tetrapeptide toxins by virtue of the production of the Hm2 polypeptide. The cells can continue to grow on medium containing the isolated toxin. Nontransformed cells do not express the Hm2 polypeptide and are rapidly killed by the toxin the pathogen produces. The net effect is a tissue culture containing only transformed cells, which can then be regenerated by known methods to form transformed shoots and even whole plants.

DETAILED DESCRIPTION OF THE INVENTION

Overview

The present invention is drawn to compositions and methods for providing disease resistance in plants. The present invention includes the sequence of the Hm2 polynucleotide (SEQ ID NO: 1), and the sequence of the Hm2 polypeptide (SEQ ID NO: 2).

In plants, the polynucleotide can be used to stably transform a plant cell or culture and regenerate plants from the transformed cell. The fertile transformed plants are capable of producing transformed progeny that express the Hm2 polynucleotide product.

The present invention also provides compositions and methods for modulating (i.e., increasing or decreasing) the level of polypeptides of the present invention in plants. In particular, the polypeptides of the present invention can be expressed temporally or spatially, e.g., at developmental stages, in tissues, and/or in quantities, which are uncharacteristic of non-recombinantly engineered plants. Thus, the present invention provides utility in such exemplary applications as disease resistance.

The present invention also provides isolated nucleic acid comprising polynucleotides of sufficient length and complementarity to a gene of the present invention to use as probes or amplification primers in the detection, quantitation, or isolation of gene transcripts. For example, isolated nucleic acids of the present invention can be used as probes in detecting deficiencies in the level of mRNA in screenings for desired transgenic plants, for detecting mutations in the gene (e.g., substitutions, deletions, or additions), for monitoring up regulation of expression or changes in enzyme activity in screening assays of compounds, for detection of any number of allelic variants (polymorphisms) of the gene, or for use as molecular markers in plant breeding programs. The isolated nucleic acids of the present invention can also be used for recombinant expression of their encoded polypeptides, or for use as immunogens in the preparation and/or screening of antibodies. The isolated nucleic acids of the present invention can also be employed for use in sense or antisense suppression of one or more genes of the present invention in a host cell, tissue, or plant. Attachment of chemical agents, which bind, intercalate, cleave and/or crosslink to the isolated nucleic acids of the present invention can also be used to modulate transcription or translation.

The present invention also provides isolated proteins comprising a polypeptide of the present invention (e.g., preproenzyme, proenzyme, or enzymes). The present invention also provides proteins comprising at least one epitope from a polypeptide of the present invention. The proteins of the present invention can be employed in assays for enzyme agonists or antagonists of enzyme function, or for use as immunogens or antigens to obtain antibodies specifically immunoreactive with a protein of the present invention. Such antibodies can be used in assays for expression levels, for identifying and/or isolating nucleic acids of the present invention from expression libraries, or for purification of polypeptides of the present invention.

Definitions

Units, prefixes, and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range and include each integer within the defined range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. The terms defined below are more fully defined by reference to the specification as a whole.

The term "cyclic tetrapeptide toxin" includes all toxins that are similar in structure to the HC toxin (HCT), that is, they all contain in addition to three usual (simple or modified) and variable amino acids, at least one of which is in the D-configuration, a fixed and rather unusual epoxide a-amino acid, Aeo. The structure of Aeo, as described earlier for HCT, is 2-amino-9,10-epoxy-8-oxodecanoic acid. Both the terminal epoxide and the vicinal 8-carbonyl (ketone) groups of Aeo are required for the biological activity of HCT (Kim, et al., *Physiol Mol Plant Pathol* 30, 433–440 (1987)). All of the known cyclic tetrapeptide toxins occur naturally and are being produced by fungi. For example: Apicidin, with the structure cyclo(L-N-O-Methyl-Tryptophan-L-Isoleucine-D-pipecolic acid-L-Aeo), was obtained from a collection of Fusarium species isolated from Costa Rica (Darkan-Rattray et al., *Proc Natl Acad Sci* 93: 13143–13147 (1996)). Chlamydocin, with the structure cyclo(Aib-L-Phe-D-Pro-L-Aeo), is produced by a cosmopolitan soil-inhabiting fungus, *Diheterospora chlamysporia* (Barron, et al., A.H.S. *Can. J. Bot*. 44: 861–865 (1966). Cyl-2, with the structure cyclo (D-O-Methyl Tyr-L-Ile-L-Pip-L-Aeo), is produced by the fungus *Cylindrocladium scoparium*, a pathogen of lettuce (Hirata et al, *Agric. Biol. Chem*. 37: 955–956 (1973). Trapoxin, with the structure cyclo(L-Phe-L-Leu-D-Pip-L-Aeo), was the first toxin of this class that was shown to be inhibitory to histone deacetylases (Yoshida, et al., *Jpn J Cancer Res* 83: 324–328 (1992); Kijima et al., *J. Biol. Chem*. 268: 22429–22435 (1993)). WF-3161, with the structure cyclo(L-Phe-L-Phe-D-Pip-L-Aeo), was isolated from a soil-borne fungus *Petriella guttulata* (Umehara et al, *J. Antibiot*. 36: 478–483 (1983)).

By "amplified" is meant the construction of multiple copies of a nucleic acid sequence or multiple copies complementary to the nucleic acid sequence using at least one of the nucleic acid sequences as a template. Amplification systems include the polymerase chain reaction (PCR) system, ligase chain reaction (LCR) system, nucleic acid sequence based amplification (NASBA, Cangene, Mississauga, Ontario), Q-Beta Replicase systems, transcription-based amplification system (TAS), and strand displacement amplification (SDA). See, e.g., *Diagnostic Molecular Microbiology: Principles and Applications*, D. H. Persing et al., Ed., American Society for Microbiology, Washington, D.C. (1993). The product of amplification is termed an amplicon.

The term "antibody" includes reference to antigen binding forms of antibodies (e.g., Fab, F(ab)$_2$). The term "antibody" frequently refers to a polypeptide substantially encoded by an immunoglobulin gene or immunoglobulin genes, or fragments thereof which specifically bind and recognize an analyte (antigen). However, while various antibody fragments can be defined in terms of the digestion of an intact antibody, one of skill will appreciate that such fragments may be synthesized de novo either chemically or by utilizing recombinant DNA methodology. Thus, the term antibody, as used herein, also includes antibody fragments such as single chain Fv, chimeric antibodies (i.e., comprising constant and variable regions from different species), humanized antibodies (i.e., comprising a complementarity determining region (CDR) from a non-human source) and heteroconjugate antibodies (e.g., bispecific antibodies).

The term "antigen" includes reference to a substance to which an antibody can be generated and/or to which the antibody is specifically innmunoreactive. The specific immunoreactive sites within the antigen are known as epitopes or antigenic determinants. These epitopes can be a linear array of monomers in a polymeric composition—such as amino acids in a protein—or consist of or comprise a more complex secondary or tertiary structure. Those of skill will recognize that all immunogens (i.e., substances capable of eliciting an immune response) are antigens; however some antigens, such as haptens, are not immunogens but may be made immunogenic by coupling to a carrier molecule. An antibody immunologically reactive with a particular antigen can be generated in vivo or by recombinant methods such as selection of libraries of recombinant antibodies in phage or similar vectors. See, e.g., Huse et al., *Science* 246: 1275–1281 (1989); and Ward, et al., *Nature* 341: 544–546 (1989); and Vaughan et al., *Nature Biotech*. 14: 309–314 (1996).

As used herein, "antisense orientation" includes reference to a duplex polynucleotide sequence which is operably linked to a promoter in an orientation where the antisense strand is transcribed. The antisense strand is sufficiently complementary to an endogenous transcription product such that translation of the endogenous transcription product is often inhibited.

As used herein, "chromosomal region" includes reference to a length of a chromosome which may be measured by reference to the linear segment of DNA which it comprises. The chromosomal region can be defined by reference to two unique DNA sequences, i.e., markers.

The term "conservatively modified variants" applies to both amino acid and nucleic acid sequences. With respect to particular nucleic acid sequences, conservatively modified variants refers to those nucleic acids which encode identical or conservatively modified variants of the amino acid sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation. Every nucleic acid sequence herein which encodes a polypeptide also, by reference to the genetic code, describes every possible silent variation of the nucleic acid. One of ordinary skill will recognize that each codon in a nucleic acid (except AUG, which is ordinarily the only codon for methionine; and UGG , which is ordinarily the only codon for tryptophan) can be modified to yield a functionally identical molecule. Accordingly, each silent variation of a nucleic acid which encodes a polypeptide of the present invention is implicit in each described polypeptide sequence and is within the scope of the present invention.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Thus, any number of amino acid residues selected from the group of integers consisting of from 1 to 15 can be so altered. Thus, for example, 1, 2, 3, 4, 5, 7, or 10 alterations can be made. Conservatively modified variants typically provide similar biological activity as the unmodified polypeptide sequence from which they are derived.

For example, substrate specificity, enzyme activity, or ligand/receptor binding is generally at least 30%, 40%, 50%, 60%, 70%, 80%, or 90% of the native protein for its native substrate. Conservative substitution tables providing functionally similar amino acids are well known in the art.

The following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W). See also, Creighton (1984) Proteins W. H. Freeman and Company.

By "encoding" or "encoded", with respect to a specified nucleic acid, is meant comprising the information for translation into the specified protein. A nucleic acid encoding a protein may comprise non-translated sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code. However, variants of the universal code, such as are present in some plant, animal, and fungal mitochondria, the bacterium *Mycoplasma capricolum*, or the ciliate Macronucleus, may be used when the nucleic acid is expressed therein.

When the nucleic acid is prepared or altered synthetically, advantage can be taken of known codon preferences of the intended host where the nucleic acid is to be expressed. For example, although nucleic acid sequences of the present invention may be expressed in both monocotyledonous and dicotyledonous plant species, sequences can be modified to account for the specific codon preferences and GC content preferences of monocotyledons or dicotyledons as these preferences have been shown to differ (Murray et al. *Nucl. Acids Res.* 17: 477–498 (1989)). Thus, the maize preferred codon for a particular amino acid may be derived from known gene sequences from maize. Maize codon usage for 28 genes from maize plants are listed in Table 4 of Murray et al., supra.

As used herein "full-length sequence" in reference to a specified polynucleotide or its encoded protein means having the entire amino acid sequence of, a native (non-synthetic), endogenous, biologically active form of the specified protein. Methods to determine whether a sequence is full-length are well known in the art including such exemplary techniques as northern or western blots, primer extension, Si protection, and ribonuclease protection. See, e.g., *Plant Molecular Biology: A Laboratory Manual*, Clark, Ed., Springer-Verlag, Berlin (1997). Comparison to known full-length homologous (orthologous and/or paralogous) sequences can also be used to identify full-length sequences of the present invention. Additionally, consensus sequences typically present at the 5' and 3' untranslated regions of MRNA aid in the identification of a polynucleotide as full-length. For example, the consensus sequence ANNNN AUGG, here the underlined codon represents the N-terminal methionine, aids in determining whether the polynucleotide has a complete 5' end. Consensus sequences at the 3' end, such as polyadenylation sequences, aid in determining whether the polynucleotide has a complete 3' end.

As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous structural gene is from a species different from that from which the structural gene was derived, or, if from the same species, one or both are substantially modified from their original form. A heterologous protein may originate from a foreign species or, if from the same species, is substantially modified from its original form by deliberate human intervention.

By "host cell" is meant a cell which contains a vector and supports the replication and/or expression of the vector. Host cells may be prokaryotic cells such as *E. coli*, or eukaryotic cells such as yeast, insect, amphibian, or mammalian cells. Preferably, host cells are monocotyledonous or dicotyledonous plant cells. A particularly preferred monocotyledonous host cell is a maize host cell.

The term "hybridization complex" includes reference to a duplex nucleic acid structure formed by two single-stranded nucleic acid sequences selectively hybridized with each other.

By "immunologically reactive conditions" or "immunoreactive conditions" is meant conditions which allow an antibody, reactive to a particular epitope, to bind to that epitope to a detectably greater degree (e.g., at least 2-fold over background) than the antibody binds to substantially any other epitopes in a reaction mixture comprising the particular epitope. Immunologically reactive conditions are dependent upon the format of the antibody binding reaction and typically are those utilized in immunoassay protocols. See Harlow and Lane, *Antibodies, A Laboratory Manual*, Cold Spring Harbor Publications, New York (1988), for a description of immunoassay formats and conditions.

The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon, or transiently expressed (e.g., transfected mRNA).

The terms "isolated" refers to material, such as a nucleic acid or a protein, which is: (1) substantially or essentially free from components that normally accompany or interact with it as found in its naturally occurring environment. The isolated material optionally comprises material not found with the material in its natural environment; or (2) if the material is in its natural environment, the material has been synthetically (non-naturally) altered by deliberate human intervention to a composition and/or placed at a location in the cell (e.g., genome or subcellular organelle) not native to a material found in that environment. The alteration to yield the synthetic material can be performed on the material within or removed from its natural state. For example, a naturally occurring nucleic acid becomes an isolated nucleic acid if it is altered, or if it is transcribed from DNA which has been altered, by means of human intervention performed within the cell from which it originates. See, e.g., Compounds and Methods for Site Directed Mutagenesis in Eukaryotic Cells, Kmiec, U.S. Pat. No. 5,565,350; In Vivo Homologous Sequence Targeting in Eukaryotic Cells; Zarling et al., PCT/US93/03868. Likewise, a naturally occurring nucleic acid (e.g., a promoter) becomes isolated if it is introduced by non-naturally occurring means to a locus of the genome not native to that nucleic acid. Nucleic acids which are "isolated" as defined herein, are also referred to as "heterologous" nucleic acids.

Unless otherwise stated, the term "Hm2 nucleic acid" is a nucleic acid of the present invention and means a nucleic acid comprising a polynucleotide of the present invention (a "Hm2 polynucleotide") encoding a Hm2 polypeptide. A "Hm2 gene" is a gene of the present invention and refers to a heterologous genomic form of a full-length Hm2 polynucleotide.

As used herein, "localized within the chromosomal region defined by and including" with respect to particular markers includes reference to a contiguous length of a chromosome delimited by and including the stated markers.

As used herein, "marker" includes reference to a locus on a chromosome that serves to identify a unique position on the chromosome. A "polymorphic marker" includes reference to a marker which appears in multiple forms (alleles) such that different forms of the marker, when they are present in a homologous pair, allow transmission of each of the chromosomes of that pair to be followed. A genotype may be defined by use of one or a plurality of markers.

As used herein, "nucleic acid" includes reference to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids).

By "nucleic acid library" is meant a collection of isolated DNA or RNA molecules which comprise and substantially represent the entire transcribed fraction of a genome of a specified organism. Construction of exemplary nucleic acid libraries, such as genomic and cDNA libraries, is taught in standard molecular biology references such as Berger and Kimmel, *Guide to Molecular Cloning Techniques, Methods in Enzymology*, Vol. 152, Academic Press, Inc., San Diego, Calif. (Berger); Sambrook et al., *Molecular Cloning—A*

*Laboratory Manual*, 2nd ed., Vol. 1–3 (1989); and *Current Protocols in Molecular Biology*, F. M. Ausubel et al., Eds., Current Protocols, a joint venture between Greene Publishing Associates, Inc. and John Wiley & Sons, Inc.

As used herein "operably linked" includes reference to a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame.

As used herein, the term "plant" includes reference to whole plants, plant organs (e.g., leaves, stems, roots, etc.), seeds and plant cells and progeny of same. Plant cell, as used herein includes, without limitation, seeds, suspension cultures, embryos, meristematic regions, callus tissue, leaves, roots, shoots, gametophytes, sporophytes, pollen, and microspores. The class of plants which can be used in the methods of the invention is generally as broad as the class of higher plants amenable to transformation techniques, including both monocotyledonous and dicotyledonous plants. A particularly preferred plant is *Zea mays*.

As used herein, "polynucleotide" includes reference to a deoxyribopolynucleotide, ribopolynucleotide, or analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide (s). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including among other things, simple and complex cells.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein, that protein is specifically reactive to antibodies elicited to the same protein but consisting entirely of naturally occurring amino acids. The terms "polypeptide", "peptide" and "protein" are also inclusive of modifications including, but not limited to, glycosylation, lipid attachment, sulfation, gamma-carboxylation of glutamic acid residues, hydroxylation and ADP-ribosylation. It will be appreciated, as is well known and as noted above, that polypeptides are not always entirely linear. For instance, polypeptides may be branched as a result of ubiquitination, and they may be circular, with or without branching, generally as a result of posttranslation events, including natural processing event and events brought about by human manipulation which do not occur naturally. Circular, branched and branched circular polypeptides may be synthesized by non-translation natural process and by entirely synthetic methods, as well. Further, this invention contemplates the use of both the methionine-containing and the methionine-less amino terminal variants of the protein of the invention.

As used herein "promoter" is intended to be a regulatory region of DNA usually comprising a TATA box capable of directing RNA polymerase II to initiate RNA synthesis at the appropriate transcription initiation site for a particular coding sequence. A promoter may additionally comprise other recognition sequences generally positioned either upstream (5') or downstream (3') to the TATA box, referred to as upstream or downstream promoter elements, respectively, which influence the transcription rate. They are typically linking via a 5' non-translated region, which may further modulate gene expression to a coding region of interest. In the same manner, the promoter elements that enable expression at the specific developmental stage, such as flowering, can be identified, isolated and used with other core promoters to confirm flowering-preferred expression. For genes in which the 5' non-translated region does not affect specificity, alternative sources of 5' non-translated leaders may be used in conjunction with these promoter elements.

A "plant promoter" is a promoter capable of initiating transcription in plant cells whether or not its origin is a plant cell. Exemplary plant promoters include, but are not limited to, those that are obtained from plants, plant viruses, and bacteria which comprise genes expressed in plant cells such Agrobacterium or Rhizobium. A "developmentally regulated" promoter initiates transcription at specific developmental stages during plant growth and development, such as flowering. The regulatory sequences of the present invention, when operably linked to a heterologous nucleotide sequence of interest and inserted into a transformation vector, enable developmentally regulated expression of the heterologous nucleotide sequence at the time of flowering.

Promoters that preferentially initiate transcription in certain tissues, such as leaves, roots, or seed are referred to as "tissue preferred". Promoters which initiate transcription only in certain tissue are referred to as "tissue specific". A "cell type" specific promoter primarily drives expression in certain cell types in one or more organs, for example, vascular cells in roots or leaves. An "inducible" or "repressible" promoter is a promoter, which is under environmental control. Examples of environmental conditions that may effect transcription by inducible promoters include anaerobic conditions or the presence of light. Developmentally regulated, tissue specific, tissue preferred, cell type specific, and inducible promoters constitute the class of "non-constitutive" promoters. A "constitutive" promoter is a promoter, which is active under most environmental conditions.

The term "Hm2 polypeptide" is a polypeptide of the present invention and refers to one or more amino acid sequences, in glycosylated or non-glycosylated form. The term is also inclusive of fragments, variants, homologs, alleles or precursors (e.g., preproproteins or proproteins) thereof. A "Hm2 protein" is a protein of the present invention and comprises a Hm2 polypeptide.

As used herein "recombinant" includes reference to a cell or vector, that has been modified by the introduction of a heterologous nucleic acid or that the cell is derived from a cell so modified. Thus, for example, recombinant cells express genes that are not found in identical form within the native (non-recombinant) form of the cell or express native genes that are otherwise abnormally expressed, under-expressed or not expressed at all as a result of deliberate human intervention. The term "recombinant" as used herein does not encompass the alteration of the cell or vector by naturally occurring events (e.g., spontaneous mutation, natural transformation/transduction/transposition) such as those occurring without deliberate human intervention.

As used herein, a "recombinant expression cassette" is a nucleic acid construct, generated recombinantly or synthetically, with a series of specified nucleic acid elements which permit transcription of a particular nucleic acid in a host cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid to be transcribed, and a promoter.

The term "residue" or "amino acid residue" or "amino acid" are used interchangeably herein to refer to an amino acid that is incorporated into a protein, polypeptide, or peptide (collectively "protein"). The amino acid may be a naturally occurring amino acid and, unless otherwise limited, may encompass known analogs of natural amino acids that can function in a similar manner as naturally occurring amino acids.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 80% sequence identity, preferably 90% sequence identity, and most preferably 100% sequence identity (i.e., complementary) with each other.

The term "specifically reactive", includes reference to a binding reaction between an antibody and a protein having an epitope recognized by the antigen binding site of the antibody. This binding reaction is determinative of the presence of a protein having the recognized epitope amongst the presence of a heterogeneous population of proteins and other biologics. Thus, under designated immunoassay conditions, the specified antibodies bind to an analyte having the recognized epitope to a substantially greater degree (e.g., at least 2-fold over background) than to substantially all other analytes lacking the epitope which are present in the sample.

Specific binding to an antibody under such conditions may require an antibody that is selected for its specificity for a particular protein. For example, antibodies raised to the polypeptides of the present invention can be selected from to obtain antibodies specifically reactive with polypeptides of the present invention. The proteins used as immunogens can be in native conformation or denatured so as to provide a linear epitope.

A variety of immunoassay formats may be used to select antibodies specifically reactive with a particular protein (or other analyte). For example, solid-phase ELISA immunoassays are routinely used to select monoclonal antibodies specifically immunoreactive with a protein. See Harlow and Lane, *Antibodies, A Laboratory Manual*, Cold Spring Harbor Publications, New York. (1988), for a description of immunoassay formats and conditions that can be used to determine selective reactivity.

The terms "stringent conditions" or "stringent hybridization conditions" includes reference to conditions under which a probe will hybridize to its target sequence, to a detectably greater degree than other sequences (e.g., at least 2-fold over background).

Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 1000 nucleotides in length, optionally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60°C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2× SSC (20× SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1× SSC at 55 to 60° C. Exemplary high stringency conditions include hybridization in 50% formamide, 1 M NaCl, 1% SDS at 37° C., and a wash in 0.1× SSC at 60 to 65° C.

Specificity is typically the function of post-hybridization washes, the critical factors being the ionic strength and temperature of the final wash solution. For DNA-DNA hybrids, the $T_m$ can be approximated from the equation of Meinkoth and Wahl, *Anal. Biochem.*, 138:267–284 (1984): $T_m=81.5°$ C.$+16.6(\log M)+0.41(\%GC)-0.61(\%$ form$)-500/$L; where M is the molarity of monovalent cations, %GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, New York (1993); and *Current Protocols in Molecular Biology*, Chapter 2, Ausubel, et al., Eds., Greene Publishing and Wiley-Interscience, New York (1995).

As used herein, "transgenic plant" includes reference to a plant which comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

As used herein, "vector" includes reference to a nucleic acid used in transfection of a host cell and into which can be inserted a polynucleotide. Vectors are often replicons. Expression vectors permit transcription of a nucleic acid inserted therein.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" means includes reference to a contiguous and specified segment of a polynucleotide sequence, wherein the polynucleotide sequence may be compared to a reference sequence and wherein the portion of the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well-known in the art.

Optimal alignment of sequences for comparison may be conducted by the local homology algorithm of Smith and Waterman, *Adv. Appl. Math.* 2: 482 (1981); by the homology alignment algorithm of Needleman and Wunsch, *J. Mol. Biol.* 48: 443 (1970); by the search for similarity method of Pearson and Lipman, *Proc. Natl. Acad. Sci.* 85: 2444 (1988); by computerized implementations of these algorithms, including, but not limited to: CLUSTAL in the PC/Gene program by Intelligenetics, Mountain View, Calif., GAP, BESTFIT, BLAST, FASTA, and TFASTA in the Wisconsin Genetics Software Package, Genetics Computer Group (GCG), 575 Science Dr., Madison, Wis., USA; the CLUSTAL program is well described by Higgins and Sharp, *Gene* 73: 237–244 (1988); Higgins and Sharp, CABIOS 5: 151–153 (1989); Corpet, et al., *Nucleic Acids Research* 16: 10881–90 (1988); Huang, et al., *Computer Applications in the Biosciences* 8: 155–65 (1992), and Pearson, et al., *Methods in Molecular Biology* 24: 307–331 (1994). The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, *Current Protocols in Molecular Biology*, Chapter 19, Ausubel, et al., Eds., Greene Publishing and Wiley-Interscience, New York (1995).

Unless otherwise stated, sequence identity/similarity values provided herein refer to the value obtained using the BLAST 2.0 suite of programs using default parameters. Altschul et al., *Nucleic Acids Res.* 25:3389–3402 (1997). Software for performing BLAST analyses is publicly available, e.g., through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) *Proc. Natl. Acad. Sci. USA* 89:10915).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance.

BLAST searches assume that proteins can be modeled as random sequences. However, many real proteins comprise regions of nonrandom sequences which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, *Comput. Chem.*, 17:149–163 (1993)) and XNU (Claverie and States, *Comput. Chem.*, 17:191–201 (1993)) low-complexity filters can be employed alone or in combination.

(c) As used herein, "sequence identity" or "identity" in the context of two nucleic acid or polypeptide sequences includes reference to the residues in the two sequences which are the same when aligned for maximum correspondence over a s specified comparison window. When percentage of sequence identity is used in reference to proteins it is recognized that residue positions which are not identical often differ by conservative amino acid substitutions, where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences which differ by such conservative substitutions are said to have "sequence similarity" or "similarity". Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, Computer Applic. Biol Sci., 4: 11–17 (1988) e.g., as implemented in the program PC/GENE (Intelligenetics, Mountain View, Calif., USA).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

(e) (i) The term "substantial identity" of polynucleotide sequences means that a polynucleotide comprises a sequence that has at least 70% sequence identity, preferably at least 80%, more preferably at least 90% and most preferably at least 95%, compared to a reference sequence using one of the alignment programs described using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of at least 60%, more preferably at least 70%, 80%, 90%, and most preferably at least 95%.

Another indication that nucleotide sequences are substantially identical is if two molecules hybridize to each other under stringent conditions. However, nucleic acids which do not hybridize to each other under stringent conditions are still substantially identical if the polypeptides which they encode are substantially identical. This may occur, e.g., when a copy of a nucleic acid is created using the maximum codon degeneracy permitted by the genetic code. One indication that two nucleic acid sequences are substantially identical is that the polypeptide which the first nucleic acid encodes is immunologically cross reactive with the polypeptide encoded by the second nucleic acid.

(e) (ii) The terms "substantial identity" in the context of a peptide indicates that a peptide comprises a sequence with at least 70% sequence identity to a reference sequence, preferably 80%, more preferably 85%, most preferably at least 90% or 95% sequence identity to the reference sequence over a specified comparison window. Optionally, optimal alignment is conducted using the homology alignment algorithm of Needleman and Wunsch, *J. Mol. Biol.* 48: 443 (1970). An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides which are "substantially similar" share sequences as noted above except that residue positions which are not identical may differ by conservative amino acid changes.

Nucleic Acids

The present invention provides, among other things, isolated nucleic acids of RNA, DNA, and analogs and/or chimeras thereof, comprising a polynucleotide of the present invention.

A polynucleotide of the present invention is inclusive of:

(a) a polynucleotide encoding a polypeptide of SEQ ID NO: 2 and conservatively modified and polymorphic variants thereof, including exemplary polynucleotides of SEQ ID NO: 1;

(b) a polynucleotide which is the product of amplification from a *Zea mays* nucleic acid library using primer pairs which selectively hybridize under stringent conditions to loci within a polynucleotide selected from the group consisting of SEQ ID NO: 1, wherein the polynucleotide has substantial sequence identity to a polynucleotide selected from the group consisting of SEQ ID NO: 1;

(c) a polynucleotide which selectively hybridizes to a polynucleotide of (a) or (b);

(d) a polynucleotide having a specified sequence identity with polynucleotides of (a), (b), or (c);

(e) a polynucleotide encoding a protein having a specified number of contiguous amino acids from a prototype polypeptide, wherein the protein is specifically recognized by antisera elicited by presentation of the protein and wherein the protein does not detectably immunoreact to antisera which has been fully immunosorbed with the protein;

(f) complementary sequences of polynucleotides of (a), (b), (c), (d), or (e); and (g) a polynucleotide comprising at least a specific number of contiguous nucleotides from a polynucleotide of (a), (b), (c), (d), (e), or (f).

A. Polynucleotides Encoding A Polypeptide of the Present Invention or Conservatively Modified or Polymorphic Variants Thereof As indicated in (a), above, the present invention provides isolated nucleic acids comprising a polynucleotide of the present invention, wherein the polynucleotide encodes a polypeptide of the present invention, or conservatively modified or polymorphic variants thereof. Accordingly, the present invention includes polynucleotides of SEQ ID NO: 1, and silent variations of polynucleotides encoding a polypeptide of SEQ ID NO: 2. The present invention further provides isolated nucleic acids comprising polynucleotides encoding conservatively modified variants of a polypeptide of SEQ ID NO: 2. Conservatively modified variants can be used to generate or select antibodies immunoreactive to the non-variant polypeptide. Additionally, the present invention further provides isolated nucleic acids comprising polynucleotides encoding one or more allelic (polymorphic) variants of polypeptides/polynucleotides. Polymorphic variants are frequently used to follow segregation of chromosomal regions in, for example, marker assisted selection methods for crop improvement.

B. Polynucleotides Amplified from a Zea mays Nucleic Acid Library As indicated in (b), above, the present invention provides an isolated nucleic acid comprising a polynucleotide of the present invention, wherein the polynucleotides are amplified from a Zea Mays nucleic acid library. Zea Mays lines B73, PHRE1, A632, BMS-P2#10, W23, and Mo17 are known and publicly available. Other publicly known and available maize lines can be obtained from the Maize Genetics Cooperation (Urbana, Ill.). The nucleic acid library may be a cDNA library, a genomic library, or a library generally constructed from nuclear transcripts at any stage of intron processing. cDNA libraries can be normalized to increase the representation of relatively rare cDNAs. In optional embodiments, the cDNA library is constructed using a full-length cDNA synthesis method. Examples of such methods include Oligo-Capping (Maruyama, K. and Sugano, S. *Gene* 138: 171–174, 1994), Biotinylated CAP Trapper (Carninci, P., Kvan, C., et al. *Genomics* 37: 327–336, 1996), and CAP Retention Procedure (Edery, E., Chu, L. L., et al. *Molecular and Cellular Biology* 15: 3363–3371, 1995). cDNA synthesis is often catalyzed at 50–55° C. to prevent formation of RNA secondary structure. Examples of reverse transcriptases that are relatively stable at these temperatures are SuperScript II Reverse Transcriptase (Life Technologies, Inc.), AMV Reverse Transcriptase (Boehringer Mannheim) and RetroAmp Reverse Transcriptase (Epicentre). Rapidly growing tissues, or rapidly dividing cells are preferably used as mRNA sources.

The present invention also provides subsequences of the polynucleotides of the present invention. A variety of subsequences can be obtained using primers which selectively hybridize under stringent conditions to at least two sites within a polynucleotide of the present invention, or to two sites within the nucleic acid which flank and comprise a polynucleotide of the present invention, or to a site within a polynucleotide of the present invention and a site within the nucleic acid which comprises it. Primers are chosen to selectively hybridize, under stringent hybridization conditions, to a polynucleotide of the present invention. Generally, the primers are complementary to a subsequence of the target nucleic acid which they amplify. As those skilled in the art will appreciate, the sites to which the primer pairs will selectively hybridize are chosen such that a single contiguous nucleic acid can be formed under the desired amplification conditions. In optional embodiments, the primers will be constructed so that they selectively hybridize under stringent conditions to a sequence (or its complement) within the target nucleic acid which comprises the codon encoding the carboxy or amino terminal amino acid residue (i.e., the 3' terminal coding region and 5' terminal coding region, respectively) of the polynucleotides of the present invention. Optionally within these embodiments, the primers will be constructed to selectively hybridize entirely within the coding region of the target polynucleotide of the present invention such that the product of amplification of a cDNA target will consist of the coding region of that cDNA. The primer length in nucleotides is selected from the group of integers consisting of from at least 15 to 50. Thus, the primers can be at least 15, 18, 20, 25, 30, 40, or 50 nucleotides in length. Those of skill will recognize that a lengthened primer sequence can be employed to increase specificity of binding (i.e., annealing) to a target sequence. A non-annealing sequence at the 5' end of a primer (a "tail") can be added, for example, to introduce a cloning site at the terminal ends of the amplicon.

The amplification products can be translated using expression systems well known to those of skill in the art and as discussed, infra. The resulting translation products can be confirmed as polypeptides of the present invention by, for example, assaying for the appropriate catalytic activity (e.g., specific activity and/or substrate specificity), or verifying the presence of one or more linear epitopes which are specific to a polypeptide of the present invention. Methods for protein synthesis from PCR derived templates are known in the art and available commercially. See, e.g., Amersham Life Sciences, Inc, Catalog '97, p.354.

Methods for obtaining 5' and/or 3' ends of a vector insert are well known in the art. See, e.g., RACE (Rapid Amplification of Complementary Ends) as described in Frohman, M. A., in PCR Protocols: A Guide to Methods and Applications, M. A. Innis, D. H. Gelfand, J. J. Sninsky, T. J. White, Eds. (Academic Press, Inc., San Diego), pp. 28–38 (1990)); see also, U.S. Pat. No. 5,470,722, and *Current Protocols in Molecular Biology*, Unit 15.6, Ausubel, et al., Eds, Greene Publishing and Wiley-Interscience, New York (1995); Frohman and Martin, *Techniques* 1:165 (1989).

C. Polynucleotides Which Selectively Hybridize to a Polynucleotide of (A) or (B)

As indicated in (c), above, the present invention provides isolated nucleic acids comprising polynucleotides of the present invention, wherein the polynucleotides selectively hybridize, under selective hybridization conditions, to a polynucleotide of sections (A) or (B) as discussed above. Thus, the polynucleotides of this embodiment can be used for isolating, detecting, and/or quantifying nucleic acids comprising the polynucleotides of (A) or (B). For example, polynucleotides of the present invention can be used to identify, isolate, or amplify partial or full-length clones in a deposited library. In some embodiments, the polynucleotides are genomic or cDNA sequences isolated or otherwise complementary to a cDNA from a dicot or monocot nucleic acid library. Exemplary species of monocots and dicots include, but are not limited to: corn, canola, soybean, cotton, wheat, sorghum, sunflower, oats, sugar cane, millet, barley, and rice. Optionally, the cDNA library comprises at least 80% full-length sequences, preferably at least 85% or 90% full-length sequences, and more preferably at least 95% full-length sequences. The cDNA libraries can be normalized to increase the representation of rare sequences. Low stringency hybridization conditions are typically, but not exclusively, employed with sequences having a reduced sequence identity relative to complementary sequences. Moderate and high stringency conditions can optionally be employed for sequences of greater identity. Low stringency conditions allow selective hybridization of sequences having about 70% sequence identity and can be employed to identify orthologous or paralogous sequences.

D. Polynucleotides Having a Specific Sequence Identity with the Polynucleotides of (A), (B) or (C)

As indicated in (d), above, the present invention provides isolated nucleic acids comprising polynucleotides of the present invention, wherein the polynucleotides have a specified identity at the nucleotide level to a polynucleotide as disclosed above in sections (A), (B), or (C), above. The percentage of identity to a reference sequence is at least 60% and, rounded upwards to the nearest integer, can be expressed as an integer selected from the group of integers consisting of from 60 to 99. Thus, for example, the percentage of identity to a reference sequence can be at least 70%, 75%, 80%, 85%, 90%, or 95%.

Optionally, the polynucleotides of this embodiment will encode a polypeptide that will share an epitope with a polypeptide encoded by the polynucleotides of sections (A), (B), or (C). Thus, these polynucleotides encode a first polypeptide which elicits production of antisera comprising antibodies which are specifically reactive to a second polypeptide encoded by a polynucleotide of (A), (B), or (C). However, the first polypeptide does not bind to antisera raised against itself when the antisera has been fully immunosorbed with the first polypeptide. Hence, the polynucleotides of this embodiment can be used to generate antibodies for use in, for example, the screening of expression libraries for nucleic acids comprising polynucleotides of (A), (B), or (C), or for purification of, or in immunoassays for, polypeptides encoded by the polynucleotides of (A), (B), or (C). The polynucleotides of this embodiment embrace nucleic acid sequences which can be employed for selective hybridization to a polynucleotide encoding a polypeptide of the present invention.

Screening polypeptides for specific binding to antisera can be conveniently achieved using peptide display libraries. This method involves the screening of large collections of peptides for individual members having the desired function or structure. Antibody screening of peptide display libraries is well known in the art. The displayed peptide sequences can be from 3 to 5000 or more amino acids in length, frequently from 5–100 amino acids long, and often from about 8 to 15 amino acids long. In addition to direct chemical synthetic methods for generating peptide libraries, several recombinant DNA methods have been described. One type involves the display of a peptide sequence on the surface of a bacteriophage or cell. Each bacteriophage or cell contains the nucleotide sequence encoding the particular displayed peptide sequence. Such methods are described in PCT patent publication Nos. 91/17271, 91/18980, 91/19818, and 93/08278. Other systems for generating libraries of peptides have aspects of both in vitro chemical synthesis and recombinant methods. See, PCT Patent publication Nos. 92/05258, 92/14843, and 96/19256. See also, U.S. Pat. Nos 5,658,754; and 5,643,768. Peptide display libraries, vectors, and screening kits are commercially available from such suppliers as Invitrogen (Carlsbad, Calif.).

E. Polynucleotides Encoding a Protein Having a Subsequence from a Prototype Polypeptide and is Cross-Reactive to the Prototype Polypeptide As indicated in (e), above, the present invention provides isolated nucleic acids comprising polynucleotides of the present invention, wherein the polynucleotides encode a protein having a subsequence of contiguous amino acids from a prototype polypeptide of the present invention such as are provided in (a), above. The length of contiguous amino acids from the prototype polypeptide is selected from the group of integers consisting of from at least 10 to the number of amino acids within the prototype sequence. Thus, for example, the polynucleotide can encode a polypeptide having a subsequence having at least 10, 15, 20, 25, 30, 35, 40, 45, or 50, contiguous amino acids from the prototype polypeptide. Further, the number of such subsequences encoded by a polynucleotide of the instant embodiment can be any integer selected from the group consisting of from 1 to 20, such as 2, 3, 4, or 5. The subsequences can be separated by any integer of nucleotides from 1 to the number of nucleotides in the sequence such as at least 5, 10, 15, 25, 50, 100, or 200 nucleotides.

The proteins encoded by polynucleotides of this embodiment, when presented as an immunogen, elicit the production of polyclonal antibodies which specifically bind to a prototype polypeptide such as but not limited to, a polypeptide encoded by the polynucleotide of (a) or (b), above. Generally, however, a protein encoded by a polynucleotide of this embodiment does not bind to antisera raised against the prototype polypeptide when the antisera has been fully immunosorbed with the prototype polypeptide. Methods of making and assaying for antibody binding specificity/affinity are well known in the art. Exemplary immunoassay formats include ELISA, competitive immunoassays, radioimmunoassays, Western blots, indirect immunofluorescent assays and the like.

In a preferred assay method, fully immunosorbed and pooled antisera which is elicited to the prototype polypeptide can be used in a competitive binding assay to test the protein. The concentration of the prototype polypeptide required to inhibit 50% of the binding of the antisera to the prototype polypeptide is determined. If the amount of the protein required to inhibit binding is less than twice the amount of the prototype protein, then the protein is said to specifically bind to the antisera elicited to the immunogen. Accordingly, the proteins of the present invention embrace allelic variants, conservatively modified variants, and minor recombinant modifications to a prototype polypeptide.

A polynucleotide of the present invention optionally encodes a protein having a molecular weight as the non-glycosylated protein within 20% of the molecular weight of the full-length non-glycosylated polypeptides of the present invention. Molecular weight can be readily determined by SDS-PAGE under reducing conditions. Optionally, the molecular weight is within 15% of a full length polypeptide of the present invention, more preferably within 10% or 5%, and most preferably within 3%, 2%, or 1% of a full length polypeptide of the present invention.

Optionally, the polynucleotides of this embodiment will encode a protein having a specific enzymatic activity at least 50%, 60%, 80%, or 90% of a cellular extract comprising the native, endogenous full-length polypeptide of the present invention. Further, the proteins encoded by polynucleotides of this embodiment will optionally have a substantially similar affinity constant ($K_m$) and/or catalytic activity (i.e., the microscopic rate constant, $k_{cat}$) as the native endogenous, full-length protein. Those of skill in the art will recognize that $k_{cat}/K_m$ value determines the specificity for competing substrates and is often referred to as the specificity constant. Proteins of this embodiment can have a $k_{cat}/K_m$ value at least 10% of a full-length polypeptide of the present invention as determined using the endogenous substrate of that polypeptide. Optionally, the $k_{cat}/K_m$ value will be at least 20%, 30%, 40%, 50%, and most preferably at least 60%, 70%, 80%, 90%, or 95% the $k_{cat/Km}$ value of the full-length polypeptide of the present invention. Determination of $k_{cat}$, $K_m$, and $k_{cat}/K_m$ can be determined by any number of means well known to those of skill in the art. For example, the initial rates (i.e., the first 5% or less of the reaction) can be determined using rapid mixing and sampling techniques (e.g., continuous-flow, stopped-flow, or rapid quenching techniques), flash photolysis, or relaxation methods (e.g., temperature jumps) in conjunction with such exemplary methods of measuring as spectrophotometry, spectrofluorimetry, nuclear magnetic resonance, or radioactive procedures. Kinetic values are conveniently obtained using a Lineweaver-Burk or Eadie-Hofstee plot.

F. Polynucleotides Complementary to the Polynucleotides of (A)–(E)

As indicated in (f), above, the present invention provides isolated nucleic acids comprising polynucleotides complementary to the polynucleotides of paragraphs A–E, above. As those of skill in the art will recognize, complementary sequences base-pair throughout the entirety of their length with the polynucleotides of sections (A)–(E) (i.e., have 100% sequence identity over their entire length). Complementary bases associate through hydrogen bonding in double stranded nucleic acids. For example, the following base pairs are complementary: guanine and cytosine; adenine and thymine; and adenine and uracil.

G. Polynucleotides Which are Subsequences of the Polynucleotides of (A)–(F)

As indicated in (g), above, the present invention provides isolated nucleic acids comprising polynucleotides which comprise at least 15 contiguous bases from the polynucleotides of sections (A) through (F) as discussed above. The length of the polynucleotide is given as an integer selected from the group consisting of from at least 15 to the length of the nucleic acid sequence from which the polynucleotide is a subsequence of. Thus, for example, polynucleotides of the present invention are inclusive of polynucleotides comprising at least 15, 20, 25, 30, 40, 50, 60, 75, or 100 contiguous nucleotides in length from the polynucleotides of (A)–(F). Optionally, the number of such subsequences encoded by a polynucleotide of the instant embodiment can be any integer selected from the group consisting of from 1 to 20, such as 2, 3, 4, or 5. The subsequences can be separated by any integer of nucleotides from 1 to the number of nucleotides in the sequence such as at least 5, 10, 15, 25, 50, 100, or 200 nucleotides.

The subsequences of the present invention can comprise structural characteristics of the sequence from which it is derived. Alternatively, the subsequences can lack certain structural characteristics of the larger sequence from which it is derived. For example, a subsequence from a polynucleotide encoding a polypeptide having at least one linear epitope in common with a prototype polypeptide sequence as provided in (a), above, may encode an epitope in common with the prototype sequence. Alternatively, the subsequence may not encode an epitope in common with the prototype sequence but can be used to isolate the larger sequence by, for example, nucleic acid hybridization with the sequence from which it's derived. Subsequences can be used to modulate or detect gene expression by introducing into the subsequences compounds which bind, intercalate, cleave and/or crosslink to nucleic acids. Exemplary compounds include acridine, psoralen, phenanthroline, naphthoquinone, daunomycin or chloroethylaminoaryl conjugates.

Construction of Nucleic Acids

The isolated nucleic acids of the present invention can be made using (a) standard recombinant methods, (b) synthetic techniques, or combinations thereof. In some embodiments, the polynucleotides of the present invention will be cloned, amplified, or otherwise constructed from a monocot. In preferred embodiments the monocot is Zea mays.

The nucleic acids may conveniently comprise sequences in addition to a polynucleotide of the present invention. For example, a multi-cloning site comprising one or more endonuclease restriction sites may be inserted into the nucleic acid to aid in isolation of the polynucleotide. Also, translatable sequences may be inserted to aid in the isolation of the translated polynucleotide of the present invention. For example, a hexa-histidine marker sequence provides a convenient means to purify the proteins of the present invention. A polynucleotide of the present invention can be attached to a vector, adapter, or linker for cloning and/or expression of a polynucleotide of the present invention. Additional sequences may be added to such cloning and/or expression sequences to optimize their function in cloning and/or expression, to aid in isolation of the polynucleotide, or to improve the introduction of the polynucleotide into a cell. Typically, the length of a nucleic acid of the present invention less the length of its polynucleotide of the present invention is less than 20 kilobase pairs, often less than 15 kb, and frequently less than 10 kb. Use of cloning vectors, expression vectors, adapters, and linkers is well known and extensively described in the art. For a description of various nucleic acids see, for example, Stratagene Cloning Systems, Catalogs 1995, 996, 1997 (La Jolla, Calif.); and, Amersham Life Sciences, Inc, Catalog '97 (Arlington Heights, Ill.).

A. Recombinant Methods for Constructing Nucleic Acids

The isolated nucleic acid compositions of this invention, such as RNA, cDNA, genomic DNA, or a hybrid thereof, can be obtained from plant biological sources using any number of cloning methodologies known to those of skill in the art. In some embodiments, oligonucleotide probes which selectively hybridize, under stringent conditions, to the polynucleotides of the present invention are used to identify the desired sequence in a cDNA or genomic DNA library. While isolation of RNA, and construction of cDNA and genomic libraries is well known to those of ordinary skill in the art, the following highlights some of the methods employed.

A1. mRNA Isolation and Purification

Total RNA from plant cells comprises such nucleic acids as mitochondrial RNA, chloroplastic RNA, rRNA, tRNA, hnRNA and mRNA. Total RNA preparation typically involves lysis of cells and removal of proteins, followed by precipitation of nucleic acids. Extraction of total RNA from plant cells can be accomplished by a variety of means. Frequently, extraction buffers include a strong detergent such as SDS and an organic denaturant such as guanidinium isothiocyanate, guanidine hydrochloride or phenol. Following total RNA isolation, poly(A)$^+$ mRNA is typically purified from the remainder RNA using oligo(dT) cellulose. Exemplary total RNA and mRNA isolation protocols are described in *Plant Molecular Biology: A Laboratory Manual*, Clark, Ed., Springer-Verlag, Berlin (1997); and, *Current Protocols in Molecular Biology*, Ausubel, et al., Eds., Greene Publishing and Wiley-Interscience, New York (1995). Total RNA and mRNA isolation kits are commercially available from vendors such as Stratagene (La Jolla, Calif.), Clonetech (Palo Alto, Calif.), Pharmacia (Piscataway, N.J.), and 5'-3' (Paoli Inc., PA). See also, U.S. Pat. Nos 5,614,391; and, 5,459,253. The mRNA can be fractionated into populations with size ranges of about 0.5, 1.0, 1.5, 2.0, 2.5 or 3.0 kb. The cDNA synthesized for each of these fractions can be size selected to the same size range as its mRNA prior to vector insertion. This method helps eliminate truncated cDNA formed by incompletely reverse transcribed mRNA.

A2. Construction of a cDNA Library

Construction of a CDNA library generally entails five steps. First, first strand cDNA synthesis is initiated from a poly(A)$^+$ mRNA template using a poly(dT) primer or random hexanucleotides. Second, the resultant RNA-DNA hybrid is converted into double stranded cDNA, typically by reaction with a combination of RNAse H and DNA polymerase I (or Klenow fragment). Third, the termini of the double stranded cDNA are ligated to adaptors. Ligation of the adaptors can produce cohesive ends for cloning. Fourth, size selection of the double stranded cDNA eliminates excess adaptors and primer fragments, and eliminates partial cDNA molecules due to degradation of mRNAs or the failure of reverse transcriptase to synthesize complete first strands. Fifth, the cDNAs are ligated into cloning vectors and packaged. cDNA synthesis protocols are well known to the skilled artisan and are described in such standard references as: *Plant Molecular Biology: A Laboratory Manual*, Clark, Ed., Springer-Verlag, Berlin (1997); and, *Current Protocols in Molecular Biology*, Ausubel, et al., Eds., Greene Publishing and Wiley-Interscience, New York (1995). cDNA synthesis kits are available from a variety of commercial vendors such as Stratagene or Pharmacia.

A number of cDNA synthesis protocols have been described which provide substantially pure full-length cDNA libraries. Substantially pure full-length cDNA libraries are constructed to comprise at least 90%, and more preferably at least 93% or 95% full-length inserts amongst clones containing inserts. The length of insert in such libraries can be from 0 to 8, 9, 10, 11, 12, 13, or more kilobase pairs. Vectors to accommodate inserts of these sizes are known in the art and available commercially. See, e.g., Stratagene's lambda ZAP Express (cDNA cloning vector with 0 to 12 kb cloning capacity).

An exemplary method of constructing a greater than 95% pure full-length cDNA library is described by Carninci et al., *Genomics*, 37:327–336 (1996). In that protocol, the cap-structure of eukaryotic mRNA is chemically labeled with biotin. By using streptavidin-coated magnetic beads, only the full-length first-strand cDNA/mRNA hybrids are selectively recovered after RNase I treatment. The method provides a high yield library with an unbiased representation of the starting mRNA population. Other methods for producing full-length libraries are known in the art. See, e.g., Edery et al., *Mol. Cell Biol.*, 15(6):3363–3371 (1995); and, PCT Application WO 96/34981.

A3. Normalized or Subtracted cDNA Libraries

A non-normalized cDNA library represents the mRNA population of the tissue it was made from. Since unique clones are out-numbered by clones derived from highly expressed genes their isolation can be laborious. Normalization of a cDNA library is the process of creating a library in which each clone is more equally represented.

A number of approaches to normalize cDNA libraries are known in the art. One approach is based on hybridization to genomic DNA. The frequency of each hybridized cDNA in the resulting normalized library would be proportional to that of each corresponding gene in the genomic DNA. Another approach is based on kinetics. If cDNA reannealing follows second-order kinetics, rarer species anneal less rapidly and the remaining single-stranded fraction of cDNA becomes progressively more normalized during the course of the hybridization. Specific loss of any species of cDNA, regardless of its abundance, does not occur at any Cot value. Construction of normalized libraries is described in Ko, *Nucl. Acids. Res.*, 18(19):5705–5711 (1990); Patanjali et al., *Proc. Natl. Acad. U.S.A.*, 88:1943–1947 (1991); U.S. Pat. Nos. 5,482,685, and 5,637,685. In an exemplary method described by Soares et al., normalization resulted in reduction of the abundance of clones from a range of four orders of magnitude to a narrow range of only 1 order of magnitude. *Proc. Natl. Acad. Sci. USA*, 91:9228–9232 (1994).

Subtracted cDNA libraries are another means to increase the proportion of less abundant cDNA species. In this procedure, cDNA prepared from one pool of mRNA is depleted of sequences present in a second pool of mRNA by hybridization. The cDNA:mRNA hybrids are removed and the remaining un-hybridized cDNA pool is enriched for sequences unique to that pool. See, Foote et al. in, *Plant Molecular Biology: A Laboratory Manual*, Clark, Ed., Springer-Verlag, Berlin (1997); Kho and Zarbl, *Technique*, 3(2):58–63 (1991); Sive and St. John, *Nucl. Acids Res.*, 16(22):10937 (1988); *Current Protocols in Molecular Biology*, Ausubel, et al., Eds., Greene Publishing and Wiley-Interscience, New York (1995); and, Swaroop et al., *Nucl. Acids Res.*, 19)8):1954 (1991). cDNA subtraction kits are commercially available. See, e.g., PCR-Select (Clontech, Palo Alto, Calif.).

A4. Construction of a Genomic Library

To construct genomic libraries, large segments of genomic DNA are generated by random fragmentation, e.g. using restriction endonucleases, and are ligated with vector DNA to form concatemers that can be packaged into the appropriate vector. Methodologies to accomplish these ends, and sequencing methods to verify the sequence of nucleic acids are well known in the art. Examples of appropriate molecular biological techniques and instructions sufficient to direct persons of skill through many construction, cloning, and screening methodologies are found in Sambrook, et al., *Molecular Cloning: A Laboratory Manual*, 2nd Ed., Cold Spring Harbor Laboratory Vols. 1–3 (1989), Methods in Enzymology, Vol. 152: *Guide to Molecular Cloning Techniques*, Berger and Kimmel, Eds., San Diego: Academic Press, Inc. (1987), *Current Protocols in Molecular Biology*, Ausubel, et al., Eds., Greene Publishing and Wiley-Interscience, New York (1995); *Plant Molecular Biology: A Laboratory Manual*, Clark, Ed., Springer-Verlag, Berlin (1997). Kits for construction of genomic libraries are also commercially available.

A5. Nucleic Acid Screening and Isolation Methods

The cDNA or genomic library can be screened using a probe based upon the sequence of a polynucleotide of the present invention such as those disclosed herein. Probes may be used to hybridize with genomic DNA or cDNA sequences to isolate homologous genes in the same or different plant species. Those of skill in the art will appreciate that various degrees of stringency of hybridization can be employed in the assay; and either the hybridization or the wash medium can be stringent. As the conditions for hybridization become more stringent, there must be a greater degree of complementarity between the probe and the target for duplex formation to occur. The degree of stringency can be controlled by temperature, ionic strength, pH and the presence of a partially denaturing solvent such as formamide. For example, the stringency of hybridization is conveniently varied by changing the polarity of the reactant solution through manipulation of the concentration of formamide within the range of 0% to 50%. The degree of complementarity (sequence identity) required for detectable binding will vary in accordance with the stringency of the hybridization medium and/or wash medium. The degree of complementarity will optimally be 100 percent; however, it should be understood that minor sequence variations in the probes and primers may be compensated for by reducing the stringency of the hybridization and/or wash medium.

The nucleic acids of interest can also be amplified from nucleic acid samples using amplification techniques. For instance, polymerase chain reaction (PCR) technology can be used to amplify the sequences of polynucleotides of the present invention and related genes directly from genomic DNA or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes. Examples of techniques sufficient to direct persons of skill through in vitro amplification methods are found in Berger, Sambrook, and Ausubel, as well as Mullis et al., U.S. Pat. No. 4,683,202 (1987); and, PCR *Protocols A Guide to Methods and Applications*, Innis et al., Eds., Academic Press Inc., San Diego, Calif. (1990). Commercially available kits for genomic PCR amplification are known in the art. See, e.g., Advantage-GC Genomic PCR Kit (Clontech). The T4 gene 32 protein (Boehringer Mannheim) can be used to improve yield of long PCR products.

PCR-based screening methods have also been described. Wilfinger et al. describe a PCR-based method in which the longest cDNA is identified in the first step so that incomplete clones can be eliminated from study. *BioTechniques*, 22(3): 481–486 (1997). In that method, a primer pair is synthesized with one primer annealing to the 5' end of the sense strand of the desired cDNA and the other primer to the vector. Clones are pooled to allow large-scale screening. By this procedure, the longest possible clone is identified amongst candidate clones. Further, the PCR product is used solely as a diagnostic for the presence of the desired cDNA and does not utilize the PCR product itself. Such methods are particularly effective in combination with a full-length cDNA construction methodology, above.

B. Synthetic Methods for Constructing Nucleic Acids

The isolated nucleic acids of the present invention can also be prepared by direct chemical synthesis by methods such as the phosphotriester method of Narang et al., *Meth. Enzymol.* 68: 90–99 (1979); the phosphodiester method of Brown et al., *Meth. Enzymol.* 68: 109–151 (1979); the diethylphosphoramidite method of Beaucage et al., *Tetra. Lett.* 22: 1859–1862 (1981); the solid phase phosphoramidite triester method described by Beaucage and Caruthers, *Tetra. Letts.* 22(20): 1859–1862 (1981), e.g., using an automated synthesizer, e.g., as described in Needham-VanDevanter et al., *Nucleic Acids Res.*, 12: 6159–6168 (1984); and, the solid support method of U.S. Pat. No. 4,458,066. Chemical synthesis generally produces a single stranded ligonucleotide. This may be converted into double stranded DNA by hybridization with a complementary sequence, or by polymerization with a DNA polymerase using the single strand as a template. One of skill will recognize that while chemical synthesis of DNA is best employed for sequences of about 100 bases or less, longer sequences may be obtained by the ligation of shorter sequences.

Expression Cassettes

The present invention further provides recombinant expression cassettes comprising a nucleic acid of the present invention. A nucleic acid sequence coding for the desired polynucleotide of the present invention, for example a cDNA or a genomic sequence encoding a full length polypeptide of the present invention, can be used to construct an expression cassette which can be introduced into the desired host cell. An expression cassette will typically comprise a polynucleotide of the present invention operably linked to transcriptional initiation regulatory sequences which will direct the transcription of the polynucleotide in the intended host cell, such as tissues of a transformed plant.

For example, plant expression vectors may include (1) a cloned plant gene under the transcriptional control of 5' and 3' regulatory sequences and (2) a dominant selectable marker. Such plant expression vectors may also contain, if desired, a promoter regulatory region (e.g., one conferring inducible or constitutive, environmentally- or developmentally-regulated, or cell- or tissue-specific/selective expression), a transcription initiation start site, a ribosome binding site, an RNA processing signal, a transcription termination site, and/or a polyadenylation signal.

A plant promoter fragment can be employed which will direct expression of a polynucleotide of the present invention in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'- promoter derived from T-DNA of *Agrobacterium tumefaciens*, the ubiquitin 1 promoter, the Smas promoter, the cinnamyl alcohol dehydrogenase promoter (U.S. Pat. No. 5,683,439), the Nos promoter, the pEmu promoter, the rubisco promoter, the GRP1-8 promoter, and other transcription initiation regions from various plant genes known to those of skill.

Alternatively, the plant promoter can direct expression of a polynucleotide of the present invention in a specific tissue or may be otherwise under more precise environmental or developmental control. Such promoters are referred to here as "inducible" promoters. Environmental conditions that may effect transcription by inducible promoters include pathogen attack, anaerobic conditions, or the presence of light. Examples of inducible promoters are the Adh1 promoter which is inducible by hypoxia or cold stress, the Hsp70 promoter which is inducible by heat stress, and the PPDK promoter which is inducible by light.

Examples of promoters under developmental control include promoters that initiate transcription only, or preferentially, in certain tissues, such as leaves, roots, fruit, seeds, or flowers. An exemplary promoter is the anther specific promoter 5126 (U.S. Pat. Nos. 5,689,049 and 5,689,051). The operation of a promoter may also vary depending on its location in the genome. Thus, an inducible promoter may become fully or partially constitutive in certain locations.

Both heterologous and non-heterologous (i.e., endogenous) promoters can be employed to direct expression of the nucleic acids of the present invention. These promoters can also be used, for example, in recombinant expression cassettes to drive expression of antisense nucleic acids to reduce, increase, or alter concentration and/or composition of the proteins of the present invention in a desired tissue. Thus, in some embodiments, the nucleic acid construct will comprise a promoter functional in a plant cell, such as in *Zea mays*, operably linked to a polynucleotide of the present invention. Promoters useful in these embodiments include the endogenous promoters driving expression of a polypeptide of the present invention.

In some embodiments, isolated nucleic acids which serve as promoter or enhancer elements can be introduced in the appropriate position (generally upstream) of a non-heterologous form of a polynucleotide of the present invention so as to up or down regulate expression of a polynucleotide of the present invention. For example, endogenous promoters can be altered in vivo by mutation, deletion, and/or substitution (see, Kmiec, U.S. Pat. No. 5,565,350; Zarling et al., PCT/US93/03868), or isolated promoters can be introduced into a plant cell in the proper orientation and distance from a gene of the present invention so as to control the expression of the gene. Gene expression can be modulated under conditions suitable for plant growth so as to alter the total concentration and/or alter the composition of the polypeptides of the present invention in plant cell. Thus, the present invention provides compositions, and methods for making, heterologous promoters and/or enhancers operably linked to a native, endogenous (i.e., non-heterologous) form of a polynucleotide of the present invention.

Methods for identifying promoters with a particular expression pattern, in terms of, e.g., tissue type, cell type, stage of development, and/or environmental conditions, are well known in the art. See, e.g., *The Maize Handbook*, Chapters 114–115, Freeling and Walbot, Eds., Springer, N.Y. (1994); *Corn and Corn Improvement*, $3^{rd}$ edition, Chapter 6, Sprague and Dudley, Eds., American Society of Agronomy, Madison, Wis. (1988). A typical step in promoter isolation methods is identification of gene products that are expressed with some degree of specificity in the target tissue. Amongst the range of methodologies are: differential hybridization to cDNA libraries; subtractive hybridization; differential display; differential 2-D protein gel electrophoresis; DNA probe arrays; and isolation of proteins known to be expressed with some specificity in the target tissue. Such methods are well known to those of skill in the art. Commercially available products for identifying promoters are known in the art such as Clontech's (Palo Alto, Calif.) Universal GenomeWalker Kit.

For the protein-based methods, it is helpful to obtain the amino acid sequence for at least a portion of the identified protein, and then to use the protein sequence as the basis for preparing a nucleic acid that can be used as a probe to identify either genomic DNA directly, or preferably, to identify a cDNA clone from a library prepared from the target tissue. Once such a cDNA clone has been identified, that sequence can be used to identify the sequence at the 5' end of the transcript of the indicated gene. For differential hybridization, subtractive hybridization and differential display, the nucleic acid sequence identified as enriched in the target tissue is used to identify the sequence at the 5' end of the transcript of the indicated gene. Once such sequences are identified, starting either from protein sequences or nucleic acid sequences, any of these sequences identified as being from the gene transcript can be used to screen a genomic library prepared from the target organism. Methods for identifying and confirming the transcriptional start site are well known in the art.

In the process of isolating promoters expressed under particular environmental conditions or stresses, or in specific tissues, or at particular developmental stages, a number of genes are identified that are expressed under the desired circumstances, in the desired tissue, or at the desired stage. Further analysis will reveal expression of each particular gene in one or more other tissues of the plant. One can identify a promoter with activity in the desired tissue or condition but that do not have activity in any other common tissue.

To identify the promoter sequence, the 5' portions of the clones described here are analyzed for sequences characteristic of promoter sequences. For instance, promoter sequence elements include the TATA box consensus sequence (TATAAT), which is usually an AT-rich stretch of 5–10 bp located approximately 20 to 40 base pairs upstream of the transcription start site. Identification of the TATA box is well known in the art. For example, one way to predict the location of this element is to identify the transcription start site using standard RNA-mapping techniques such as primer extension, S1 analysis, and/or RNase protection. To confirm the presence of the AT-rich sequence, a structure-function analysis can be performed involving mutagenesis of the putative region and quantification of the mutation's effect on expression of a linked downstream reporter gene. See, e.g., *The Maize Handbook*, Chapter 114, Freeling and Walbot, Eds., Springer, New York, (1994).

In plants, further upstream from the TATA box, at positions −80 to −100, there is typically a promoter element (i.e., the CAAT box) with a series of adenines surrounding the trinucleotide G (or T) N G. J. Messing et al., in *Genetic Engineering in Plants*, Kosage, Meredith and Hollaender, Eds., pp. 221–227 1983. In maize, there is no well conserved CAAT box but there are several short, conserved protein-binding motifs upstream of the TATA box. These include motifs for the trans-acting transcription factors involved in light regulation, anaerobic induction, hormonal regulation, or anthocyanin biosynthesis, as appropriate for each gene.

Once promoter and/or gene sequences are known, a region of suitable size is selected from the genomic DNA that is 5' to the transcriptional start, or the translational start site, and such sequences are then linked to a coding sequence. If the transcriptional start site is used as the point of fusion, any of a number of possible 5' untranslated regions can be used in between the transcriptional start site and the partial coding sequence. If the translational start site at the 3' end of the specific promoter is used, then it is linked directly to the methionine start codon of a coding sequence.

If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added can be derived from, for example, the nopaline synthase or octopine synthase genes, or alternatively from another plant gene, or less preferably from any other eukaryotic gene.

An intron sequence can be added to the 5' untranslated region or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold. Buchman and Berg, *Mol. Cell Biol.* 8: 4395–4405 (1988); Callis et al., *Genes Dev.* 1: 1183–1200 (1987). Such intron enhancement of gene expression is typically greatest when placed near the 5' end of the transcription unit. Use of maize introns Adh1-S intron 1, 2, and 6, the Bronze-1 intron are known in the art. See generally, *The Maize Handbook*, Chapter 116, Freeling and Walbot, Eds., Springer, N.Y. (1994).

The vector comprising the sequences from a polynucleotide of the present invention will typically comprise a marker gene which confers a selectable phenotype on plant cells. Usually, the selectable marker gene will encode antibiotic resistance, with suitable genes including genes coding for resistance to the antibiotic spectinomycin (e.g., the aada gene), the streptomycin phosphotransferase (SPT) gene coding for streptomycin resistance, the neomycin phosphotransferase (NPTII) gene encoding kanamycin or geneticin resistance, the hygromycin phosphotransferase (HPT) gene coding for hygromycin resistance, genes coding for resistance to herbicides which act to inhibit the action of acetolactate synthase (ALS), in particular the sulfonylurea-type herbicides (e.g., the acetolactate synthase (ALS) gene containing mutations leading to such resistance in particular the S4 and/or Hra mutations), genes coding for resistance to herbicides which act to inhibit action of glutamine synthase, such as phosphinothricin or basta (e.g., the bar gene), or other such genes known in the art. The bar gene encodes resistance to the herbicide basta, the nptII gene encodes resistance to the antibiotics kanamycin and geneticin, and the ALS gene encodes resistance to the herbicide chlorsulfuron.

Typical vectors useful for expression of genes in higher plants are well known in the art and include vectors derived from the tumor-inducing (Ti) plasmid of *Agrobacterium tumefaciens* described by Rogers et al., Meth. in Enzymol., 153:253–277 (1987). These vectors are plant integrating vectors in that on transformation, the vectors integrate a portion of vector DNA into the genome of the host plant. Exemplary *A. tumefaciens* vectors useful herein are plasmids pKYLX6 and pKYLX7 of Schardl et al., Gene, 61:1–11 (1987) and Berger et al., Proc. Natl. Acad. Sci. U.S.A., 86:8402–8406 (1989). Another useful vector herein is plasmid pBI101.2 that is available from Clontech Laboratories, Inc. (Palo Alto, Calif.).

A polynucleotide of the present invention can be expressed in either sense or anti-sense orientation as desired. It will be appreciated that control of gene expression in either sense or anti-sense orientation can have a direct impact on the observable plant characteristics. Antisense technology can be conveniently used to gene expression in plants. To accomplish this, a nucleic acid segment from the desired gene is cloned and operably linked to a promoter such that the anti-sense strand of RNA will be transcribed. The construct is then transformed into plants and the anti-sense strand of RNA is produced. In plant cells, it has been shown that antisense RNA inhibits gene expression by preventing the accumulation of mRNA which encodes the enzyme of interest, see, e.g., Sheehy et al., *Proc. Nat'l. Acad. Sci. (USA)* 85: 8805–8809 (1988); and Hiatt et al., U.S. Pat. No. 4,801,340.

Another method of suppression is sense suppression. Introduction of nucleic acid configured in the sense orientation has been shown to be an effective means by which to block the transcription of target genes. For an example of the use of this method to modulate expression of endogenous genes see, Napoli et al., *The Plant Cell* 2: 279–289 (1990) and U.S. Pat. No. 5,034,323.

Catalytic RNA molecules or ribozymes can also be used to inhibit expression of plant genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs. The design and use of target RNA-specific ribozymes is described in Haseloff et at., Nature 334: 585–591 (1988).

A variety of cross-linking agents, alkylating agents and radical generating species as pendant groups on polynucleotides of the present invention can be used to bind, label, detect, and/or cleave nucleic acids. For example, Vlassov, V. V., et al., *Nucleic Acids Res* (1986) 14:4065–4076, describe covalent bonding of a single-stranded DNA fragment with alkylating derivatives of nucleotides complementary to target sequences. A report of similar work by the same group is that by Knorre, D. G., et al., *Biochimie* (1985) 67:785–789. Iverson and Dervan also showed sequence-specific cleavage of single-stranded DNA mediated by incorporation of a modified nucleotide which was capable of activating cleavage (*J Am Chem Soc* (1987) 109:1241–1243). Meyer, R. B., et al., *J Am Chem Soc* (1989) 111:8517–8519, effect covalent crosslinking to a target nucleotide using an alkylating agent complementary to the single-stranded target nucleotide sequence. A photoactivated crosslinking to single-stranded oligonucleotides mediated by psoralen was disclosed by Lee, B. L., et al., *Biochemistry* (1988) 27:3197–3203. Use of crosslinking in triple-helix forming probes was also disclosed by Home, et al., *J Am Chem Soc* (1990) 112:2435–2437. Use of N4, N4-ethanocytosine as an alkylating agent to crosslink to single-stranded oligonucleotides has also been described by Webb and Matteucci, *J Am Chem Soc* (1986) 108:2764–2765; *Nucleic Acids Res* (1986) 14:7661–7674; Feteritz et al., *J. Am. Chem. Soc.* 113:4000 (1991). Various compounds to bind, detect, label, and/or cleave nucleic acids are known in the art. See, for example, U.S. Pat. Nos 5,543,507; 5,672,593; 5,484,908; 5,256,648; and, 5,681941.

Proteins

The isolated proteins of the present invention comprise a polypeptide having at least 10 amino acids encoded by any one of the polynucleotides of the present invention as discussed more fully, above, or polypeptides which are conservatively modified variants thereof. The proteins of the present invention or variants thereof can comprise any number of contiguous amino acid residues from a polypeptide of the present invention, wherein that number is selected from the group of integers consisting of from 10 to the number of residues in a full-length polypeptide of the present invention. Optionally, this subsequence of contiguous amino acids is at least 15, 20, 25, 30, 35, or 40 amino acids in length, often at least 50, 60, 70, 80, or 90 amino acids in length. Further, the number of such subsequences can be any integer selected from the group consisting of from 1 to 20, such as 2, 3, 4, or 5.

As those of skill will appreciate, the present invention includes catalytically active polypeptides of the present invention (i.e., enzymes). Catalytically active polypeptides have a specific activity of at least 20%, 30%, or 40%, and preferably at least 50%, 60%, or 70%, and most preferably at least 80%, 90%, or 95% that of the native (non-synthetic), endogenous polypeptide. Further, the substrate specificity ($k_{cat}/K_m$) is optionally substantially similar to the native (non-synthetic), endogenous polypeptide. Typically, the $K_m$ will be at least 30%, 40%, or 50%, that of the native (non-synthetic), endogenous polypeptide; and more preferably at least 60%, 70%, 80%, or 90%. Methods of assaying and quantifying measures of enzymatic activity and substrate specificity ($k_{cat}/K_m$), are well known to those of skill in the art.

Generally, the proteins of the present invention will, when presented as an immunogen, elicit production of an antibody specifically reactive to a polypeptide of the present invention. Further, the proteins of the present invention will not bind to antisera raised against a polypeptide of the present invention which has been fully immunosorbed with the same polypeptide. Immunoassays for determining binding are well known to those of skill in the art. A preferred immunoassay is a competitive immunoassay as discussed, infra. Thus, the proteins of the present invention can be employed as immunogens for constructing antibodies immunoreactive to a protein of the present invention for such exemplary utilities as immunoassays or protein purification techniques.

Expression of Proteins in Host Cells

Using the nucleic acids of the present invention, one may express a protein of the present invention in a recombinantly engineered cell such as bacteria, yeast, insect, mammalian, or preferably plant cells. The cells produce the protein in a non-natural condition (e.g., in quantity, composition, location, and/or time), because they have been genetically altered through human intervention to do so.

It is expected that those of skill in the art are knowledgeable in the numerous expression systems available for expression of a nucleic acid encoding a protein of the present invention. No attempt to describe in detail the various methods known for the expression of proteins in prokaryotes or eukaryotes will be made.

In brief summary, the expression of isolated nucleic acids encoding a protein of the present invention will typically be achieved by operably linking, for example, the DNA or cDNA to a promoter (which is either constitutive or regulatable), followed by incorporation into an expression vector. The vectors can be suitable for replication and integration in either prokaryotes or eukaryotes. Typical expression vectors contain transcription and translation terminators, initiation sequences, and promoters useful for regulation of the expression of the DNA encoding a protein of the present invention. To obtain high level expression of a cloned gene, it is desirable to construct expression vectors which contain, at the minimum, a strong promoter to direct transcription, a ribosome binding site for translational initiation, and a transcription/translation terminator. One of skill would recognize that modifications can be made to a protein of the present invention without diminishing its biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids (e.g., poly His) placed on either terminus to create conveniently located purification sequences. Restriction sites or termination codons can also be introduced.

A. Expression in Prokaryotes

Prokaryotic cells may be used as hosts for expression. Prokaryotes most frequently are represented by various strains of *E. coli*; however, other microbial strains may also be used. Commonly used prokaryotic control sequences which are defined herein to include promoters for transcription initiation, optionally with an operator, along with ribosome binding site sequences, include such commonly used promoters as the beta lactamase (penicillinase) and lactose (lac) promoter systems (Chang et al., Nature 198:1056 (1977)), the tryptophan (trp) promoter system (Goeddel et al., Nucleic Acids Res. 8:4057 (1980)) and the lambda derived P L promoter and N-gene ribosome binding site (Shimatake et al., Nature 292:128 (1981)). The inclusion of selection markers in DNA vectors transfected in *E. coli* is also useful. Examples of such markers include genes specifying resistance to ampicillin, tetracycline, or chloramphenicol.

The vector is selected to allow introduction into the appropriate host cell. Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA. Expression systems for expressing a protein of the present invention are available using Bacillus sp. and Salmonella (Palva, et al., Gene 22: 229–235 (1983); Mosbach, et al., Nature 302: 543–545 (1983)).

B. Expression in Eukaryotes

A variety of eukaryotic expression systems such as yeast, insect cell lines, plant and mammalian cells, are known to those of skill in the art. As explained briefly below, the present invention can be expressed in these eukaryotic systems. In some embodiments, transformed/transfected plant cells, as discussed infra, are employed as expression systems for production of the proteins of the instant invention.

Synthesis of heterologous proteins in yeast is well known. Sherman, F., et al., *Methods in Yeast Genetics*, Cold Spring Harbor Laboratory (1982) is a well recognized work describing the various methods available to produce the protein in yeast. Two widely utilized yeast for production of eukaryotic proteins are *Saccharomyces cerevisiae* and *Pichia pastoris*. Vectors, strains, and protocols for expression in Saccharomyces and Pichia are known in the art and available from commercial suppliers (e.g., Invitrogen). Suitable vectors usually have expression control sequences, such as promoters, including 3-phosphoglycerate kinase or alcohol oxidase, and an origin of replication, termination sequences and the like as desired.

A protein of the present invention, once expressed, can be isolated from yeast by lysing the cells and applying standard protein isolation techniques to the lysates. The monitoring of the purification process can be accomplished by using Western blot techniques or radioimmunoassay of other standard immunoassay techniques.

The sequences encoding proteins of the present invention can also be ligated to various expression vectors for use in transfecting cell cultures of, for instance, mammalian, insect, or plant origin. Illustrative of cell cultures useful for the production of the peptides are mammalian cells. Mammalian cell systems often will be in the form of monolayers of cells although mammalian cell suspensions may also be used. A number of suitable host cell lines capable of expressing intact proteins have been developed in the art, and include the HEK293, BHK21, and CHO cell lines. Expression vectors for these cells can include expression control sequences, such as an origin of replication, a promoter (e.g., the CMV promoter, a HSV tk promoter or pgk (phosphoglycerate kinase) promoter), an enhancer (Queen et al., *Immunol. Rev.* 89: 49 (1986)), and necessary processing information sites, such as ribosome binding sites, RNA splice sites, polyadenylation sites (e.g., an SV40 large T Ag poly A addition site), and transcriptional terminator sequences. Other animal cells useful for production of proteins of the present invention are available, for instance, from the American Type Culture Collection.

Appropriate vectors for expressing proteins of the present invention in insect cells are usually derived from the SF9 baculovirus. Suitable insect cell lines include mosquito larvae, silkworm, armyworm, moth and Drosophila cell lines such as a Schneider cell line (See, Schneider, *J. Embryol. Exp. Morphol.* 27: 353–365 (1987).

As with yeast, when higher animal or plant host cells are employed, polyadenlyation or transcription terminator sequences are typically incorporated into the vector. An example of a terminator sequence is the polyadenlyation sequence from the bovine growth hormone gene. Sequences for accurate splicing of the transcript may also be included. An example of a splicing sequence is the VP1 intron from SV40 (Sprague, et al.,; *J. Virol.* 45: 773–781 (1983)). Additionally, gene sequences to control replication in the host cell may be incorporated into the vector such as those found in bovine papilloma virus type-vectors. Saveria-Campo, M., Bovine Papilloma Virus DNA a Eukaryotic Cloning Vector in *DNA Cloning Vol. II a Practical Approach*, D. M. Glover, Ed., IRL Press, Arlington, Va. pp. 213–238 (1985).

Transfection/Transformation of Cells

The method of transformation/transfection is not critical to the instant invention; various methods of transformation or transfection are currently available. As newer methods are available to transform crops or other host cells they may be directly applied. Accordingly, a wide variety of methods have been developed to insert a DNA sequence into the genome of a host cell to obtain the transcription and/or translation of the sequence to effect phenotypic changes in the organism. Thus, any method which provides for effective transformation/transfection may be employed.

A. Plant Transformation

A DNA sequence coding for the desired polynucleotide of the present invention, for example a cDNA or a genomic sequence encoding a full length protein, will be used to construct a recombinant expression cassette which can be introduced into the desired plant.

The compositions and methods of the present invention can be used in any transformation protocol. Such transformation protocols may vary depending on the type of plant or plant cell, i.e. monocot or dicot, targeted for transformation. Suitable methods of transforming plant cells include microinjection (Crossway et al. (1986) *Biotechniques* 4:320–334), electroporation (Riggs et al (1986) *Proc. Natl. Acad. Sci. USA*, 83:5602–5606, Agrobacterium mediated transformation (Hinchee et 25 al. (1988) *Biotechnology*, 6:915–921), direct gene transfer (Paszkowski et al. (1984) *EMBO J.*, 3:2717–2722), and ballistic particle acceleration (see, for example, Sanford et al, U.S. Pat. No. 4,945,050; and McCabe et al (1988) *Biotechnology*, 6:923–926). Also see, Weissinger et al. (1988) *Annual Rev. Genet.*, 22:421477; Sanford et al. (1987) *Particulate Science and Technology*, 5:27–37 (onion); Christou et al. (1988) *Plant Physiol.* 87:671–674(soybean); McCabe et al. (1988) *Bio/Technology*, 6:923–926 (soybean); Datta et al (1990) *Biotechnology*, 8:736–740(rice); Klein et al (1988) *Proc. natl. Acad. Sci. USA*, 8S:4305A309 (maize); Klein et al. (1988) *Biotechnology*, 6:559–563 (maize); Klein et al. (1988) *Plant Physiol.*, 91:440–444(maize); and Fromm et al. (1990) *Biotechnology*, 8:833–839; Hooydaas-Van Slogteren & Hooykaas (1984) *Nature* London), 311:763–764; Bytebier et al (1987) *Proc. Natl. Acad. Sci. USA*, 84:5345–5349 (Liliaceae); De Wet et al. (1985) In *The Experimental Manipulation of Ovule Tissues*, ed. G. P. Chapman et al., pp.197–209. Longman, N.Y. (pollen); Kaeppler et al. (1990) *Plant Cell Reports*, 9:415–418; and Kaeppler et al. (1992) *Theor. Appl. Genet.*, 84:560–566 (whisker-mediated transformation); D'Halluin et al. (1992) *Plant Cell*, 4:1495–1505 (electroporation); Li et al (1993) *Plant Cell Reports*, 12:250–255 and Christou and Ford (1995) *Annals of Botany*, 75:407A13 (rice); Osjoda et al. (1996) *Nature Biotechnology*, 14:745–750 (maize via *Agrobacterium tumefaciens*); all of which are herein incorporated by reference.

The plant plastid can also be transformed directly. Stable transformation of targeting of the DNA to the plastid genome through homologous recombination. Additionally, plastid transformation can be accomplished by transactivation of a silent plastid-borne transgene by tissue-specific expression of a nuclear-encoded and plastid-directed RNA polymerase. Such a system has been reported in McBride et al. (1994) *Proc. natl. Acad. Sci., USA*, 91:7301–7305 and herein incorporated by reference. Where the transformation protocol is directed to plastid transformation, the marker genes are optimized for expression in the plant plastid.

B. Transfection of Prokaryotes, Lower Eukaryotes, and Animal Cells

Animal and lower eukaryotic (e.g., yeast) host cells are competent or rendered competent for transfection by various means. There are several well-known methods of introducing DNA into animal cells. These include: calcium phosphate precipitation, fusion of the recipient cells with bacterial protoplasts containing the DNA, treatment of the recipient cells with liposomes containing the DNA, DEAE dextran, electroporation, biolistics, and micro-injection of the DNA directly into the cells. The transfected cells are cultured by means well known in the art. Kuchler, R. J., *Biochemical Methods in Cell Culture and Virology*, Dowden, Hutchinson and Ross, Inc. (1977).

Synthesis of Proteins

The proteins of the present invention can be constructed using non-cellular synthetic methods. Solid phase synthesis of proteins of less than about 50 amino acids in length may be accomplished by attaching the C-terminal amino acid of the sequence to an insoluble support followed by sequential addition of the remaining amino acids in the sequence. Techniques for solid phase synthesis are described by Barany and Merrifield, Solid-Phase Peptide Synthesis, pp. 3–284 in *The Peptides: Analysis, Synthesis, Biology. Vol. 2: Special Methods in Peptide Synthesis*, Part A.; Merrifield, et al.,*J. Am. Chem. Soc.* 85: 2149–2156 (1963), and Stewart et al., *Solid Phase Peptide Synthesis*, 2nd ed., Pierce Chem. Co., Rockford, Ill. (1984). Proteins of greater length may be synthesized by condensation of the amino and carboxy termini of shorter fragments. Methods of forming peptide bonds by activation of a carboxy terminal end (e.g., by the use of the coupling reagent N,N'-dicycylohexylcarbodiimide)) is known to those of skill.

Purification of Proteins

The proteins of the present invention may be purified by standard techniques well known to those of skill in the art. Recombinantly produced proteins of the present invention can be directly expressed or expressed as a fusion protein. The recombinant protein is purified by a combination of cell lysis (e.g., sonication, French press) and affinity chromatography. For fusion products, subsequent digestion of the fusion protein with an appropriate proteolytic enzyme releases the desired recombinant protein.

The proteins of this invention, recombinant or synthetic, may be purified to substantial purity by standard techniques well known in the art, including detergent solubilization, selective precipitation with such substances as ammonium sulfate, column chromatography, immunopurification methods, and others. See, for instance, R. Scopes, *Protein*

*Purification: Principles and Practice*, Springer-Verlag: New York (1982); Deutscher, *Guide to Protein Purification*, Academic Press (1990). For example, antibodies may be raised to the proteins as described herein. Purification from *E. coli* can be achieved following procedures described in U.S. Pat. No. 4,511,503. The protein may then be isolated from cells expressing the protein and further purified by standard protein chemistry techniques as described herein. Detection of the expressed protein is achieved by methods known in the art and include, for example, radioimmunoassays, Western blotting techniques or immunoprecipitation.

Transgenic Plant Regeneration

Transformed plant cells which are derived by any of the above transformation techniques can be cultured to regenerate a whole plant which possesses the transformed genotype. Such regeneration techniques often rely on manipulation of certain phytohormones in a tissue culture growth medium, typically relying on a biocide and/or herbicide marker which has been introduced together with a polynucleotide of the present invention. For transformation and regeneration of maize see, Gordon-Kamm et al., *The Plant Cell*, 2:603–618 (1990).

Plants cells transformed with a plant expression vector can be regenerated, e.g., from single cells, callus tissue or leaf discs according to standard plant tissue culture techniques. It is well known in the art that various cells, tissues, and organs from almost any plant can be successfully cultured to regenerate an entire plant. Plant regeneration from cultured protoplasts is described in Evans et al., *Protoplasts Isolation and Culture, Handbook of Plant Cell Culture*, Macmillilan Publishing Company, New York, pp. 124–176 (1983); and Binding, *Regeneration of Plants, Plant Protoplasts*, CRC Press, Boca Raton, pp. 21–73 (1985).

The regeneration of plants containing the foreign gene introduced by Agrobacterium from leaf explants can be achieved as described by Horsch et al., *Science*, 227:1229–1231 (1985). In this procedure, transformants are grown in the presence of a selection agent and in a medium that induces the regeneration of shoots in the plant species being transformed as described by Fraley et al., *Proc. Natl. Acad. Sci. (U.S.A.)*, 80:4803 (1983). This procedure typically produces shoots within two to four weeks and these transformant shoots are then transferred to an appropriate root-inducing medium containing the selective agent and an antibiotic to prevent bacterial growth. Transgenic plants of the present invention may be fertile or sterile.

Regeneration can also be obtained from plant callus, explants, organs, or parts thereof. Such regeneration techniques are described generally in Klee et al., *Ann. Rev. of Plant Phys.* 38: 467–486 (1987). The regeneration of plants from either single plant protoplasts or various explants is well known in the art. See, for example, *Methods for Plant Molecular Biology*, A. Weissbach and H. Weissbach, eds., Academic Press, Inc., San Diego, Calif. (1988). This regeneration and growth process includes the steps of selection of transformant cells and shoots, rooting the transformant shoots and growth of the plantlets in soil. For maize cell culture and regeneration see generally, *The Maize Handbook*, Freeling and Walbot, Eds., Springer, New York (1994); *Corn and Corn Improvement*, $3^{rd}$ edition, Sprague and Dudley Eds., American Society of Agronomy, Madison, Wis. (1988).

One of skill will recognize that after the recombinant expression cassette is stably incorporated in transgenic plants and confirmed to be operable, it can be introduced into other plants by sexual crossing. Any of a number of standard breeding techniques can be used, depending upon the species to be crossed.

In vegetatively propagated crops, mature transgenic plants can be propagated by the taking of cuttings or by tissue culture techniques to produce multiple identical plants. Selection of desirable transgenics is made and new varieties are obtained and propagated vegetatively for commercial use. In seed propagated crops, mature transgenic plants can be self crossed to produce a homozygous inbred plant. The inbred plant produces seed containing the newly introduced heterologous nucleic acid. These seeds can be grown to produce plants that would produce the selected phenotype.

Parts obtained from the regenerated plant, such as flowers, seeds, leaves, branches, fruit, and the like are included in the invention, provided that these parts comprise cells comprising the isolated nucleic acid of the present invention. Progeny and variants, and mutants of the regenerated plants are also included within the scope of the invention, provided that these parts comprise the introduced nucleic acid sequences.

Transgenic plants expressing the selectable marker can be screened for transmission or the nucleic acid of the present invention by, for example, standard immunoblot and DNA detection techniques. Transgenic lines are also typically evaluated on levels of expression of the heterologous nucleic acid. Expression at the RNA level can be determined initially to identify and quantitate expression-positive plants. Standard techniques for RNA analysis can be employed and include PCR amplification assays using oligonucleotide primers designed to amplify only the heterologous RNA templates and solution hybridization assays using heterologous nucleic acid-specific probes. The RNA-positive plants can then be analyzed for protein expression by Western immunoblot analysis using the specifically reactive antibodies of the present invention. In addition, in situ hybridization and immunocytochernistry according to standard protocols can be done using heterologous nucleic acid specific polynucleotide probes and antibodies, respectively, to localize sites of expression within transgenic tissue. Generally, a number of transgenic lines are usually screened for the incorporated nucleic acid to identify and select plants with the most appropriate expression profiles.

A preferred embodiment is a transgenic plant that is homozygous for the added heterologous nucleic acid; i.e., a transgenic plant that contains two added nucleic acid sequences, one gene at the same locus on each chromosome of a chromosome pair. A homozygous transgenic plant can be obtained by sexually mating (selling) a heterozygous transgenic plant that contains a single added heterologous nucleic acid, germinating some of the seed produced and analyzing the resulting plants produced for altered expression of a polynucleotide of the present invention relative to a control plant (i.e., native, non-transgenic). Back-crossing to a parental plant and out-crossing with a non- transgenic plant are also contemplated.

Modulating Polypeptide Levels and/or Composition

The present invention further provides a method for modulating (i.e., increasing or decreasing) the concentration or composition of the polypeptides of the present invention in a plant or part thereof. Modulation can be effected by increasing or decreasing the concentration and/or the composition (i.e., the ratio of the polypeptides of the present invention) in a plant. The method comprises introducing into a plant cell with a recombinant expression cassette comprising a polynucleotide of the present invention as described above to obtain a transformed plant cell, culturing the transformed plant cell under plant cell growing conditions, and inducing or repressing expression of a polynucleotide of the present invention in the plant for a time sufficient to modulate concentration and/or composition in the plant or plant part.

In some embodiments, the content and/or composition of polypeptides of the present invention in a plant may be modulated by altering, in vivo or in vitro, the promoter of a gene to up- or down-regulate gene expression. In some embodiments, the coding regions of native genes of the present invention can be altered via substitution, addition, insertion, or deletion to decrease activity of the encoded enzyme. See, e.g., Kmiec, U.S. Pat. No. 5,565,350; Zarling et al., PCT/US93/03868. And in some embodiments, an isolated nucleic acid (e.g., a vector) comprising a promoter sequence is transfected into a plant cell. Subsequently, a plant cell comprising the promoter operably linked to a polynucleotide of the present invention is selected for by means known to those of skill in the art such as, but not limited to, Southern blot, DNA sequencing, or PCR analysis using primers specific to the promoter and to the gene and detecting amplicons produced therefrom. A plant or plant part altered or modified by the foregoing embodiments is grown under plant forming conditions for a time sufficient to modulate the concentration and/or composition of polypeptides of the present invention in the plant. Plant forming conditions are well known in the art and discussed briefly, supra.

In general, concentration or composition is increased or decreased by at least 5%, 10%, 20%, 30%, 40%, 50%, 60%, 70%, 80%, or 90% relative to a native control plant, plant part, or cell lacking the aforementioned recombinant expression cassette. Modulation in the present invention may occur during and/or subsequent to growth of the plant to the desired stage of development. Modulating nucleic acid expression temporally and/or in particular tissues can be controlled by employing the appropriate promoter operably linked to a polynucleotide of the present invention in, for example, sense or antisense orientation as discussed in greater detail, supra. Induction of expression of a polynucleotide of the present invention can also be controlled by exogenous administration of an effective amount of inducing compound. Inducible promoters and inducing compounds which activate expression from these promoters are well known in the art. In preferred embodiments, the polypeptides of the present invention are modulated in monocots, particularly maize.

Molecular Markers

The present invention provides a method of genotyping a plant comprising a polynucleotide of the present invention. Optionally, the plant is a monocot, such as maize or sorghum. Genotyping provides a means of distinguishing homologs of a chromosome pair and can be used to differentiate segregants in a plant population. Molecular marker methods can be used for phylogenetic studies, characterizing genetic relationships among crop varieties, identifying crosses or somatic hybrids, localizing chromosomal segments affecting monogenic traits, map based cloning, and the study of quantitative inheritance. See, e.g., *Plant Molecular Biology: A Laboratory Manual*, Chapter 7, Clark, Ed., Springer-Verlag, Berlin (1997). For molecular marker methods, see generally, The DNA Revolution by Andrew H. Paterson 1996 (Chapter 2) in: Genome Mapping in Plants (ed. Andrew H. Paterson) by Academic Press/R. G. Landis Company, Austin, Tex., pp.7–21.

The particular method of genotyping in the present invention may employ any number of molecular marker analytic techniques such as, but not limited to, restriction fragment length polymorphisms (RFLPs). RFLPs are the product of allelic differences between DNA restriction fragments resulting from nucleotide sequence variability. As is well known to those of skill in the art, RFLPs are typically detected by extraction of genomic DNA and digestion with a restriction enzyme. Generally, the resulting fragments are separated according to size and hybridized with a probe; single copy probes are preferred. Restriction fragments from homologous chromosomes are revealed. Differences in fragment size among alleles represent an RFLP. Thus, the present invention further provides a means to follow segregation of a gene or nucleic acid of the present invention as well as chromosomal sequences genetically linked to these genes or nucleic acids using such techniques as RFLP analysis. Linked chromosomal sequences are within 50 centiMorgans (cM), often within 40 or 30 cM, preferably within 20 or 10 cM, more preferably within 5, 3, 2, or 1 cM of a gene of the present invention.

In the present invention, the nucleic acid probes employed for molecular marker mapping of plant nuclear genomes selectively hybridize, under selective hybridization conditions, to a gene encoding a polynucleotide of the present invention. In preferred embodiments, the probes are selected from polynucleotides of the present invention. Typically, these probes are cDNA probes or restriction-enzyme treated (e.g., Pst I) genomic clones. The length of the probes is discussed in greater detail, supra, but are typically at least 15 bases in length, more preferably at least 20, 25, 30, 35, 40, or 50 bases in length. Generally, however, the probes are less than about 1 kilobase in length. Preferably, the probes are single copy probes that hybridize to a unique locus in a haploid chromosome complement. Some exemplary restriction enzymes employed in RFLP mapping are EcoRI, EcoRv, and SstI. As used herein the term "restriction enzyme" includes reference to a composition that recognizes and, alone or in conjunction with another composition, cleaves at a specific nucleotide sequence.

The method of detecting an RFLP comprises the steps of (a) digesting genomic DNA of a plant with a restriction enzyme; (b) hybridizing a nucleic acid probe, under selective hybridization conditions, to a sequence of a polynucleotide of the present of said genomic DNA; (c) detecting therefrom a RFLP. Other methods of differentiating polymorphic (allelic) variants of polynucleotides of the present invention can be had by utilizing molecular marker techniques well known to those of skill in the art including such techniques as: 1) single stranded conformation analysis (SSCA); 2) denaturing gradient gel electrophoresis (DGGE); 3) RNase protection assays; 4) allele-specific oligonucleotides (ASOs); 5) the use of proteins which recognize nucleotide mismatches, such as the *E. coli* mutS protein; and 6) allele-specific PCR. Other approaches based on the detection of mismatches between the two complementary DNA strands include clamped denaturing gel electrophoresis (CDGE); heteroduplex analysis (HA); and chemical mismatch cleavage (CMC). Exemplary polymorphic variants are provided in Table I, supra. Thus, the present invention further provides a method of genotyping comprising the steps of contacting, under stringent hybridization conditions, a sample suspected of comprising a polynucleotide of the present invention with a nucleic acid probe.

Generally, the sample is a plant sample; preferably, a sample suspected of comprising a maize polynucleotide of the present invention (e.g., gene, mRNA). The nucleic acid probe selectively hybridizes, under stringent conditions, to a subsequence of a polynucleotide of the present invention comprising a polymorphic marker. Selective hybridization of the nucleic acid probe to the polymorphic marker nucleic acid sequence yields a hybridization complex. Detection of the hybridization complex indicates the presence of that polymorphic marker in the sample. In preferred embodiments, the nucleic acid probe comprises a polynucleotide of the present invention.

UTRs and Codon Preference

In general, translational efficiency has been found to be regulated by specific sequence elements in the 5' non-coding or untranslated region (5' UTR) of the RNA. Positive sequence motifs include translational initiation consensus sequences (Kozak, *Nucleic Acids Res.* 15:8125 (1987)) and the 7-methylguanosine cap structure (Drummond et al., *Nucleic Acids Res.* 13:7375 (1985)). Negative elements include stable intramolecular 5' UTR stem-loop structures (Muesing et al., Cell 48:691 (1987)) and AUG sequences or short open reading frames preceded by an appropriate AUG in the 5' UTR (Kozak, supra, Rao et al., *Mol. and Cell. Biol.* 8:284 (1988)). Accordingly, the present invention provides 5' and/or 3' UTR regions for modulation of translation of heterologous coding sequences.

Further, the polypeptide-encoding segments of the polynucleotides of the present invention can be modified to alter codon usage. Altered codon usage can be employed to alter translational efficiency and/or to optimize the coding sequence for expression in a desired host such as to optimize the codon usage in a heterologous sequence for expression in maize. Codon usage in the coding regions of the polynucleotides of the present invention can be analyzed statistically using commercially available software packages such as "Codon Preference" available from the University of Wisconsin Genetics Computer Group (see Devereaux et al., *Nucleic Acids Res.* 12: 387–395 (1984)) or MacVector 4.1 (Eastman Kodak Co., New Haven, Conn.). Thus, the present invention provides a codon usage frequency characteristic of the coding region of at least one of the polynucleotides of the present invention. The number of polynucleotides that can be used to determine a codon usage frequency can be any integer from 1 to the number of polynucleotides of the present invention as provided herein. Optionally, the polynucleotides will be full-length sequences. An exemplary number of sequences for statistical analysis can be at least 1, 5, 10, 20, 50, or 100.

Sequence Shuffling

More effective variants of Hm2 could be synthesized through the use of in vitro recombination (Zhang, J.-H., G. Dawes, W. P. C. Stemmer. 1997). Directed evolution of a fucosidase from a galactosidase by DNA shuffling and screening (*Proc. Natl. Acad. Sci. USA* 94:4504–4509). For example, the known homologs of Hm1 from maize and other species could be recombined using the method of DNA shuffling and screened or selected for more effective variants. The new variants could be selected or screened against a variety of HC-toxin isoforms (Rasmussen, J., R. P. Scheffer. (1988) Isolation and biological activities of four selective toxins from Helminthosporium carbonum. *Plant Physiology* 86:187–191) and related molecules, such as apicidin (Darkin-Rattray et al. (1996) Apicidin: a novel antiprotozoal agent that inhibits parasite histone deacetylase (*Proc. Natl. Acad. Sci. USA* 93:13143–13147), trapoxin (Kijima, M., M. Yoshida, K. Sugita, S. Horinouchi, T. Beppu 1993, Trapoxin, an antitumor cyclic tetrapeptide is an irreversible inhibitor of mammalian histone deacetylase, *J. Biol. Chem*. 268: 22429–22435), cyl-2 and chlamydocin (Walton, J. D., E. D. Earle, H. Stahelin, A. Grieder, A. Hirota, A. Suzuki. 1985, Reciprocal biological activities of the cyclic tetrapeptides chlamydocin and HC-toxin, *Experientia* 41:348–350) to identify the most effective enzyme/toxin combinations for uses including as a selectable marker system for transformation.

Generic and Consensus Sequences

Polynucleotides and polypeptides of the present invention further include those having: (a) a generic sequence of at least two homologous polynucleotides or polypeptides, respectively, of the present invention; and, (b) a consensus sequence of at least three homologous polynucleotides or polypeptides, respectively, of the present invention. The generic sequence of the present invention comprises each species of polypeptide or polynucleotide embraced by the generic polypeptide or polynucleotide, sequence, respectively. The individual species encompassed by a polynucleotide having an amino acid or nucleic acid consensus sequence can be used to generate antibodies or produce nucleic acid probes or primers to screen for homologs in other species, genera, families, orders, classes, phylums, or kingdoms. For example, a polynucleotide having a consensus sequences from a gene family of *Zea Mays* can be used to generate antibody or nucleic acid probes or primers to other Gramineae species such as wheat, rice, or sorghum. Alternatively, a polynucleotide having a consensus sequence generated from orthologous genes can be used to identify or isolate orthologs of other taxa. Typically, a polynucleotide having a consensus sequence will be at least 9, 10, 15, 20, 25, 30, or 40 amino acids in length, or 20, 30, 40, 50, 100, or 150 nucleotides in length. As those of skill in the art are aware, a conservative amino acid substitution can be used for amino acids which differ amongst aligned sequence but are from the same conservative substitution group as discussed above. Optionally, no more than 1 or 2 conservative amino acids are substituted for each 10 amino acid length of consensus sequence.

Similar sequences used for generation of a consensus or generic sequence include any number and combination of allelic variants of the same gene, orthologous, or paralogous sequences as provided herein. Optionally, similar sequences used in generating a consensus or generic sequence are identified using the BLAST algorithm's smallest sum probability (P(N)). Various suppliers of sequence-analysis software are listed in chapter 7 of *Current Protocols in Molecular Biology*, F. M. Ausubel et al., Eds., Current Protocols, a joint venture between Greene Publishing Associates, Inc. and John Wiley & Sons, Inc. (Supplement 30). A polynucleotide sequence is considered similar to a reference sequence if the smallest sum probability in a comparison of the test nucleic acid to the reference nucleic acid is less than about 0.1, more preferably less than about 0.01, or 0.001, and most preferably less than about 0.0001, or 0.00001. Similar polynucleotides can be aligned and a consensus or generic sequence generated using multiple sequence alignment software available from a number of commercial suppliers such as the Genetics Computer Group's (Madison, Wis.) PILEUP software, Vector NTI's (North Bethesda, Md.) ALIGNX, or Genecode's (Ann Arbor, Mich.) SEQUENCHER. Conveniently, default parameters of such software can be used to generate consensus or generic sequences.

Homology Searches

The present invention provides: 1) a machine having a memory comprising data representing a sequence of a polynucleotide or polypeptide of the present invention; 2) a data structure comprising a sequence of a polynucleotide of the present invention embodied in a computer readable medium; and 3) a process for identifying a candidate homologue of a polynucleotide of the present invention. A candidate homologue has statistically significant probability of having the same function (e.g., catalyzes the same reaction) as the reference sequence to which it's compared. Unless otherwise provided for, software, electrical, and electronics terms as used herein are as defined in The New IEEE Standard Dictionary of Electrical and Electronics Terms ($5^{th}$ edition, 1993).

The machine of the present invention is typically a digital computer. The memory of such a machine includes, but is not limited to, ROM, or RAM, or computer readable media such as, but not limited to, magnetic media such as computer disks or hard drives, or media such as CD-ROM. As those of skill in the art will be aware, the form of memory of a machine of the present invention is not a critical element of the invention and can take a variety of forms.

The process of the present invention comprises obtaining data representing a polynucleotide or polypeptide test sequence. Test sequences are generally at least 25 amino acids in length or at least 50 nucleotides in length. Optionally, the test sequence can be at least 50, 100, 150, 200, 250, 300, or 400 amino acids in length. A test polynucleotide can be at least 50, 100, 200, 300, 400, or 500 nucleotides in length. Often the test sequence will be a full-length sequence. Test sequences can be obtained from a nucleic acid of an animal or plant. Optionally, the test sequence is obtained from a plant species other than maize whose function is uncertain but will be compared to the test sequence to determine sequence similarity or sequence identity; for example, such plant species can be of the family Gramineae, such as wheat, rice, or sorghum. The test sequence data are entered into a machine, typically a computer, having a memory that contains data representing a reference sequence. The reference sequence can be the sequence of a polypeptide or a polynucleotide of the present invention and is often at least 25 amino acids or 100 nucleotides in length. As those of skill in the art are aware, the greater the sequence identity/similarity between a reference sequence of known function and a test sequence, the greater the probability that the test sequence will have the same or similar function as the reference sequence.

The machine further comprises a sequence comparison means for determining the sequence identity or similarity between the test sequence and the reference sequence. Exemplary sequence comparison means are provided for in sequence analysis software discussed previously. Optionally, sequence comparison is established using the BLAST suite of programs.

The results of the comparison between the test and reference sequences can be displayed. Generally, a smallest sum probability value (P(N)) of less than 0.1, or alternatively, less than 0.01, 0.001, 0.0001, or 0.00001 using the BLAST 2.0 suite of algorithms under default parameters identifies the test sequence as a candidate homologue (i.e., an allele, ortholog, or paralog) of the reference sequence. A nucleic acid comprising a polynucleotide having the sequence of the candidate homologue can be constructed using well known library isolation, cloning, or in vitro synthetic chemistry techniques (e.g., phosphoramidite) such as those described herein. In additional embodiments, a nucleic acid comprising a polynucleotide having a sequence represented by the candidate homologue is introduced into a plant; typically, these polynucleotides are operably linked to a promoter. Confirmation of the function of the candidate homologue can be established by operably linking the candidate homolog nucleic acid to, for example, an inducible promoter, or by expressing the antisense transcript, and analyzing the plant for changes in phenotype consistent with the presumed function of the candidate homolog. Optionally, the plant into which these nucleic acids are introduced is a monocot such as from the family Gramineae. Exemplary plants include corn, sorghum, wheat, rice, canola, alfalfa, cotton, and soybean.

Detection of Nucleic Acids

The present invention further provides methods for detecting a polynucleotide of the present invention in a nucleic acid sample suspected of containing a polynucleotide of the present invention, such as a plant cell lysate, particularly a lysate of corn. In some embodiments, a gene of the present invention or portion thereof can be amplified prior to the step of contacting the nucleic acid sample with a polynucleotide of the present invention. The nucleic acid sample is contacted with the polynucleotide to form a hybridization complex. The polynucleotide hybridizes under stringent conditions to a gene encoding a polypeptide of the present invention. Formation of the hybridization complex is used to detect a gene encoding a polypeptide of the present invention in the nucleic acid sample. Those of skill will appreciate that an isolated nucleic acid comprising a polynucleotide of the present invention should lack cross-hybridizing sequences in common with non-target genes that would yield a false positive result.

Detection of the hybridization complex can be achieved using any number of well known methods. For example, the nucleic acid sample, or a portion thereof, may be assayed by hybridization formats including but not limited to, solution phase, solid phase, mixed phase, or in situ hybridization assays. Briefly, in solution (or liquid) phase hybridizations, both the target nucleic acid and the probe or primer are free to interact in the reaction mixture. In solid phase hybridization assays, probes or primers are typically linked to a solid support where they are available for hybridization with target nucleic in solution. In mixed phase, nucleic acid intermediates in solution hybridize to target nucleic acids in solution as well as to a nucleic acid linked to a solid support. In in situ hybridization, the target nucleic acid is liberated from its cellular surroundings in such as to be available for hybridization within the cell while preserving the cellular morphology for subsequent interpretation and analysis. The following articles provide an overview of the various hybridization assay formats: Singer et al., *Biotechniques* 4(3): 230–250 (1986); Haase et al., *Methods in Virology*, Vol. VII, pp. 189–226 (1984); Wilkinson, The theory and practice of in situ hybridization in: *In situ Hybridization*, D. G. Wilkinson, Ed., IRL Press, Oxford University Press, Oxford; and *Nucleic Acid Hybridization: A Practical Approach*, Hames, B. D. and Higgins, S. J., Eds., IRL Press (1987).

Nucleic Acid Labels and Detection Methods

The means by which nucleic acids of the present invention are labeled is not a critical aspect of the present invention and can be accomplished by any number of methods currently known or later developed. Detectable labels suitable for use in the present invention include any composition detectable by spectroscopic, radioisotopic, photochemical, biochemical, immunochemical, electrical, optical or chemical means. Useful labels in the present invention include biotin for staining with labeled streptavidin conjugate, magnetic beads, fluorescent dyes (e.g., fluorescein, Texas red, rhodamine, green fluorescent protein, and the like), radiolabels (e.g., $^{3}H$, $^{125}I$, $^{35}S$, $^{14}C$, or $^{32}P$), enzymes (e.g., horse radish peroxidase, alkaline phosphatase and others commonly used in an ELISA), and colorimetric labels such as colloidal gold or colored glass or plastic (e.g., polystyrene, polypropylene, latex, etc.) beads.

Nucleic acids of the present invention can be labeled by any one of several methods typically used to detect the presence of hybridized nucleic acids. One common method of detection is the use of autoradiography using probes labeled with $^{3}H$, $^{125}I$, $^{35}S$, $^{14}C$, or $^{32}P$, or the like. The choice of radioactive isotope depends on research preferences due to ease of synthesis, stability, and half lives of the selected isotopes. Other labels include ligands which bind to anti-bodies labeled with fluorophores, chemiluminescent agents, and enzymes. Alternatively, probes can be conjugated directly with labels such as fluorophores, chemiluminescent agents or enzymes. The choice of label depends on sensitivity required, ease of conjugation with the probe, stability requirements, and available instrumentation. Labeling the nucleic acids of the present invention is readily achieved such as by the use of labeled PCR primers.

In some embodiments, the label is simultaneously incorporated during the amplification step in the preparation of the nucleic acids. Thus, for example, polymerase chain reaction (PCR) with labeled primers or labeled nucleotides will provide a labeled amplification product. In another embodiment, transcription amplification using a labeled nucleotide (e.g., fluorescein-labeled UTP and/or CTP) incorporates a label into the transcribed nucleic acids.

Non-radioactive probes are often labeled by indirect means. For example, a ligand molecule is covalently bound to the probe. The ligand then binds to an anti-ligand molecule which is either inherently detectable or covalently bound to a detectable signal system, such as an enzyme, a fluorophore, or a chemiluminescent compound. Enzymes of interest as labels will primarily be hydrolases, such as phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescers include luciferin, and 2,3-dihydrophthalazinediones, e.g., luminol. Ligands and anti-ligands may be varied widely. Where a ligand has a natural anti-ligand, namely ligands such as biotin, thyroxine, and cortisol, it can be used in conjunction with its labeled, naturally occurring anti-ligands. Alternatively, any haptenic or antigenic compound can be used in combination with an antibody.

Probes can also be labeled by direct conjugation with a label. For example, cloned DNA probes have been coupled directly to horseradish peroxidase or alkaline phosphatase. Means of detecting such labels are well known to those of skill in the art. Thus, for example, radiolabels may be detected using photographic film or scintillation counters, fluorescent markers may be detected using a photodetector to detect emitted light. Enzymatic labels are typically detected by providing the enzyme with a substrate and detecting the reaction product produced by the action of the enzyme on the substrate, and colorimetric labels are detected by simply visualizing the colored label.

Antibodies to Proteins

Antibodies can be raised to a protein of the present invention, including individual, allelic, strain, or species variants, and fragments thereof, both in their naturally occurring (full-length) forms and in recombinant forms. Additionally, antibodies are raised to these proteins in either their native configurations or in non-native configurations. Anti-idiotypic antibodies can also be generated. Many methods of making antibodies are known to persons of skill. A variety of analytic methods are available to generate a hydrophilicity profile of a protein of the present invention. Such methods can be used to guide the artisan in the selection of peptides of the present invention for use in the generation or selection of antibodies which are specifically reactive, under immunogenic conditions, to a protein of the present invention. See, e.g., J. Janin, *Nature*, 277 (1979) 491–492; Wolfenden, et al., *Biochemistry* 20(1981) 849–855; Kyte and Doolite, *J. Mol. Biol.* 157 (1982) 105–132; Rose, et al., *Science* 229 (1985) 834–838. The following discussion is presented as a general overview of the techniques available; however, one of skill will recognize that many variations upon the following methods are known.

A number of immunogens are used to produce antibodies specifically reactive with a protein of the present invention. An isolated recombinant, synthetic, or native polynucleotide of the present invention are the preferred immunogens (antigen) for the production of monoclonal or polyclonal antibodies. Polypeptides of the present invention are typically denatured, and optionally reduced, prior to formation of antibodies for screening expression libraries or other assays in which a putative protein of the present invention is expressed or denatured in a non-native secondary, tertiary, or quartenary structure.

The protein of the present invention is then injected into an animal capable of producing antibodies. Either monoclonal or polyclonal antibodies can be generated for subsequent use in immunoassays to measure the presence and quantity of the protein of the present invention. Methods of producing polyclonal antibodies are known to those of skill in the art. In brief, an immunogen (antigen), preferably a purified protein, a protein coupled to an appropriate carrier (e.g., GST, keyhole limpet hemanocyanin, etc.), or a protein incorporated into an immunization vector such as a recombinant vaccinia virus (see, U.S. Pat. No. 4,722,848) is mixed with an adjuvant and animals are immunized with the mixture. The animal's immune response to the immunogen preparation is monitored by taking test bleeds and determining the titer of reactivity to the protein of interest. When appropriately high titers of antibody to the immunogen are obtained, blood is collected from the animal and antisera are prepared. Further fractionation of the antisera to enrich for antibodies reactive to the protein is performed where desired (See, e.g., Coligan, *Current Protocols in Immunology*, Wiley/Greene, NY (1991); and Harlow and Lane, *Antibodies: A Laboratory Manual*, Cold Spring Harbor Press, NY (1989)).

Antibodies, including binding fragments and single chain recombinant versions thereof, against predetermined fragments of a protein of the present invention are raised by immunizing animals, e.g., with conjugates of the fragments with carrier proteins as described above. Typically, the immunogen of interest is a protein of at least about 5 amino acids, more typically the protein is 10 amino acids in length, preferably, 15 amino acids in length and more preferably the protein is 20 amino acids in length or greater. The peptides are typically coupled to a carrier protein (e.g., as a fusion protein), or are recombinantly expressed in an immunization vector. Antigenic determinants on peptides to which antibodies bind are typically 3 to 10 amino acids in length.

Monoclonal antibodies are prepared from cells secreting the desired antibody. Monoclonals antibodies are screened for binding to a protein from which the immunogen was derived. Specific monoclonal and polyclonal antibodies will usually have an antibody binding site with an affinity constant for its cognate monovalent antigen at least between $10^6$–$10^7$, usually at least $10^8$, preferably at least $10^9$, more preferably at least $10^{10}$, and most preferably at least $10^{11}$ liters/mole.

In some instances, it is desirable to prepare monoclonal antibodies from various mammalian hosts, such as mice, rodents, primates, humans, etc. Description of techniques for preparing such monoclonal antibodies are found in, e.g., *Basic and Clinical Immunology*, 4th ed., Stites et al., Eds., Lange Medical Publications, Los Altos, Calif., and references cited therein; Harlow and Lane, Supra; Goding, *Monoclonal Antibodies: Principles and Practice*, 2nd ed., Academic Press, New York, N.Y. (1986); and Kohler and Milstein, Nature 256: 495–497 (1975). Summarized briefly, this method proceeds by injecting an animal with an immunogen comprising a protein of the present invention. The animal is then sacrificed and cells taken from its spleen, which are fused with myeloma cells. The result is a hybrid cell or "hybridoma" that is capable of reproducing in vitro. The population of hybridomas is then screened to isolate individual clones, each of which secrete a single antibody species to the immunogen. In this manner, the individual antibody species obtained are the products of immortalized and cloned single B cells from the immune animal generated in response to a specific site recognized on the immunogenic substance.

Other suitable techniques involve selection of libraries of recombinant antibodies in phage or similar vectors (see, e.g., Huse et al., Science 246: 1275–1281 (1989); and Ward, et al., Nature 341: 544–546 (1989); and Vaughan et al., *Nature Biotechnology*, 14: 309–314 (1996)). Alternatively, high avidity human monoclonal antibodies can be obtained from transgenic mice comprising fragments of the unrearranged human heavy and light chain Ig loci (i.e., minilocus transgenic mice). Fishwild et al., *Nature Biotech.*, 14: 845–851 (1996). Also, recombinant immunoglobulins may be produced. See, Cabilly, U.S. Pat. No. 4,816,567; and Queen et al., *Proc. Nat'l Acad. Sci.* 86: 10029–10033 (1989).

The antibodies of this invention are also used for affinity chromatography in isolating proteins of the present invention. Columns are prepared, e.g., with the antibodies linked to a solid support, e.g., particles, such as agarose, SEPHADEX, or the like, where a cell lysate is passed through the column, washed, and treated with increasing concentrations of a mild denaturant, whereby purified protein are released.

The antibodies can be used to screen expression libraries for particular expression products such as normal or abnormal protein. Usually the antibodies in such a procedure are labeled with a moiety allowing easy detection of presence of antigen by antibody binding.

Antibodies raised against a protein of the present invention can also be used to raise anti-idiotypic antibodies. These are useful for detecting or diagnosing various pathological conditions related to the presence of the respective antigens.

Frequently, the proteins and antibodies of the present invention will be labeled by joining, either covalently or non-covalently, a substance which provides for a detectable signal. A wide variety of labels and conjugation techniques are known and are reported extensively in both the scientific and patent literature. Suitable labels include radionucleotides, enzymes, substrates, cofactors, inhibitors, fluorescent moieties, chemiluminescent moieties, magnetic particles, and the like.

Assays for Compounds that Modulate Enzymatic Activity or Expression

The present invention also provides means for identifying compounds that bind to (e.g., substrates), and/or increase or decrease (i.e., modulate) the enzymatic activity of, catalytically active polypeptides of the present invention. The method comprises contacting a polypeptide of the present invention with a compound whose ability to bind to or modulate enzyme activity is to be determined. The polypeptide employed will have at least 20%, preferably at least 30% or 40%, more preferably at least 50% or 60%, and most preferably at least 70% or 80% of the specific activity of the native, full-length polypeptide of the present invention (e.g., enzyme). Generally, the polypeptide will be present in a range sufficient to determine the effect of the compound, typically about 1 nM to 10 $\mu$M. Likewise, the compound will be present in a concentration of from about 1 nM to 10 $\mu$M. Those of skill will understand that such factors as enzyme concentration, ligand concentrations (i.e., substrates, products, inhibitors, activators), pH, ionic strength, and temperature will be controlled so as to obtain useful kinetic data and determine the presence of absence of a compound that binds or modulates polypeptide activity. Methods of measuring enzyme kinetics is well known in the art. See, e.g., Segel, *Biochemical Calculations*, $2^{nd}$ ed., John Wiley and Sons, New York (1976).

Use of the Present Invention for Disease Resistance in Plants

The Hm2 polynucleotides of the present invention can be inserted into the genomes of plants susceptible to disease caused by fungal pathogens utilizing a cyclic tetrapeptide toxin, by the methods outlined above. Upon expression of the Hm2 polynucleotide the plants would become resistant to the fungal pathogens.

The isolated nucleic acids of the present invention can be used to transform a broad range of plant types, particularly monocots such as the species of the family Gramineae including *Sorghum bicolor* and *Zea mays*. The isolated nucleic acid and proteins of the present invention can also be used in species from the genera: Cucurbita, Rosa, Vitis, Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Ciahorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browaalia, Glycine, Pisum, Phaseolus, Lolium, Oryza, Avena, Hordeum, Secale, and Triticum.

Use of the Present Invention for Selection of Transformants

Alternatively, the present invention can be used as a method for selection of transformants, in other words as a selectable marker. The Hm2 polynucleotide operably linked to a promoter and then transformed into a plant cell by any of the methods described above would express the Hm2 enzyme. When the plant cells are placed in the presence of a cyclic tetrapeptide, such as HC toxin, or *C. carbonum* in culture only the transformed cells would be able to grow.

Thus, growth of plant cells in the presence of the toxin or fungus favors the survival of plant cells that have been transformed to express the coding sequence that codes for one of the enzymes of this invention and degrades the toxin. When the Hm2 cassette is co-transformed with another gene of interest and then placed in the presence of a cyclic tetrapeptide toxin, this invention would allow for selection of only those plant cells that contain the gene of interest. In the past antibiotic resistance genes have been used as selectable markers. Given the current concerns by consumers and environmentalist over use of antibiotic genes and the possibility of resistant microorganisms arising due to this use, a non-antibiotic resistant selectable marker system such as the present invention, fulfills this very important need.

Although the present invention has been described in some detail by way of illustration and example for purposes of clarity of understanding, it will be obvious that certain changes and modifications may be practiced within the scope of the appended claims.

EXPERIMENTAL

Example 1

Isolation and Characterization of the Hm2 Gene, cDNA, and Polypeptide:

The susceptible maize inbreds used in this study were obtained from the following sources: Pr from Iowa State University, Ames, Iowa; K41, K44, and K61 from Kansas State University, Manhattan, Kans.; and MO21A from L. D. Dunkle, Purdue University, West Lafayette, Ind. The Hm2 tester (br2hm1Hm2) was developed from a brachytic2 mutant (br2Hm1Hm2) stock by crossing it to Pr (Br2hm1hm2) followed by self-pollination of a few resulting progeny. The disease reaction of all plants used in this study was assessed by inoculating seedlings at the 3–4 leaf stage with *C. carbonum* race 1 (Meeley, R. B., Johal, G. S., Briggs, S. P. & Walton, J. D. (1992) *Plant Cell* 4, 71–77).

DNA Extraction and Southern Blotting. Total DNA from the seedling tissue of all plant species was isolated by a miniprep method (Dellaporta, S. L, Wood, J. & Hicks, J. B. (1983) *Plant Mol Biol. Rep.* 1, 19–21). For Southern analysis, digested DNA was transferred to nylon membranes (Fisher) and hybridized in a solution containing 5× standard saline citrate (SSC), 5× Denhardt's solution, 5% Dextran sulfate, 1 mM EDTA, 2 mM Tris (pH 7.5), 0.1% SDS, and salmon sperm DNA (10 mg.ml$^{-1}$) (Johal, G. S. & Briggs, S. P. (1992) *Science* 258, 985–987). Blots were washed stringently in 2× SSC and 0.5% SDS at room temperature for 15 mm followed by three more washes for 15 mm each at 65° C. in 1× SSC, 0.2× SSC, and 0.1× SSC, each containing 0.1% SDS.

Cloning of hm2. The hm2 gene was cloned from a B73 genomic library by using a probe derived from the 3' half of the Hm1-cDNA. The hm2 allele of B73, which is recessive genetically, was subcloned in two parts into a pBluescript vector, SK+ (Stratagene): pHM216, a 1.6-kb BamHI fragment, which contained part of the hm2 polynucleotide that extends from the end of the exon 2 into the 5' end of the polynucleotide; and pHM215, a 1.5-kb BamHI/SacI fragment, which contained, in addition to exons 3, 4, and 5, some sequences from the 3' region of the hm2 polynucleotide.

DNA Sequencing and Analysis. Sequencing of both strands of both the hm2-B73 subclones, pHM216 and pHM215 was accomplished by cycle sequencing with a SequiTherm DNA Polymerase kit (Epicentre Technologies, Madison, Wis.) using the forward and reverse primers of M13. Amino acid sequence alignment was performed with the DNASTAR MEGALIGN program using a clustal method with a PAM 250 residue weight table, a gap penalty of 10, and a gap length penalty of 10.

The hm2 Allele of B73. The putative hm2 allele of B73 has been sequenced to entirety (SEQ ID NO:3; the predicted amino acid sequence can be seen in SEQ ID NO:4). In addition to sharing more than 70% identity throughout the length of the polynucleotide, the intron/exon boundaries are conserved between this polynucleotide and hm1, suggesting that the two may be structurally related by descent.

In fact, a number of additional pieces of evidence have been obtained which suggest that the hm1-homolog in question represents the hm2 gene. First, this clone is completely linked with the hm2 locus. To examine this, a backcross (BC) population was prepared that segregated 1:1 for resistant (hm1hm1Hm2hm2) vs. susceptible (hm1hm1hm2hm2) plants. The stocks used to generate this population were Pr1 (Hm1Hm1hm2hm2) and a brachytic-2 (br2) mutant, with the genotype hm1hm1Hm2Hm2. The br2 gene, which is within 0.2 cM of hm1, served as a genetic marker to segregate Hm1 out, so that the phenotypic effects of Hm2 could be discerned. One hundred and forty plants from the BC population (mentioned above) were tested for linkage with the HM215 subclone. No recombinants were found, suggesting that the clone had originated from at least within 0.7 cM of hm2. From another population (F2), in which the hm2 allele was derived from MO21A (another susceptible inbred), 100 plants representing 200 meiotic events were tested for linkage with the hm2 function. Again complete linkage was detected between our clone and the hm2 gene, indicating that if the clone is not hm2 it has come from a location that is within 0.6 cM of hm2.

Second, a major part of the gene homologous to the clone is deleted in the susceptible inbred Pr, on which the disease was first witnessed in 1938. Detailed restriction analysis in conjuction with PCR amplification experiments have demonstrated that the 5' end of the deletion lies somewhere in or around exon 2. The 3' end of the deletion in Pr remains unknown and is probably outside the 3' limit of the gene.

Third, Northern blot analysis has demonstrated a close correspondence between the induction kinetics of the clone-specific transcript and the expression pattern of Hm2-conferred resistance.

Fourth, sorghum and rice, like most monocots, contain two homologs of hm1, which occupy chromosomal locations that are syntenic with the maize hm1 and hm2 loci.

Taken together, the results and observations discussed above provide a compelling evidence that the hm1-homolog cloned is the hm2 polynucleotide. However B73, from which this hm2 clone was isolated, had never been characterized in terms of whether it contained a functional or recessive copy of the hm2 polynucleotide. To assess this, a cross was made between B73 and Pr and the resulting hybrid was self-pollinated to produce an F2 population. About a hundred plants from this progeny were planted and inoculated with *C. carbonum* race 1 when the seedlings were 2 weeks old. All resistant plants (about ¾th) were discarded and the remaining susceptible plants were re-inoculated when 7 weeks old. No resistance was encountered; the disease reaction of all of these plants was identical to that of Pr, demonstrating that the hm2 allele of B73, like that of Pr, is genetically recessive or nonfunctional. As a result of this finding, a Hm2 polynucleotide sequence was cloned from a subgenomic library prepared from the br2br2hm1hm1Hm2Hm2 tester. A near-full length cDNA clone of Hm2 was PCR amplified from this stock using a 3'

RACE protocol with a gene-specific primer (5'-TCGGCTCCTGGCTCGTCAGGAAGCTC-3'; SEQ ID NO: 5) and the adapter primer provided with the kit [GIBCO BRL]. The PCR product (1.2 kb) was cloned in a TA cloning vector (Invitrogen) and then sequenced. The 5' end of the Hm2 cDNA was PCR amplified using an RT-PCR approach. A 5' end gene specific primer was designed based on information obtained from two Pioneer express sequence tags. These express sequence tags were: CLSAE95R and CNAMK28R. The primer sequence was: 5'-GGAAGGGGAGAAGAGCTAGAG-3'. (SEQ ID NO: 6) This primer (SEQ ID NO: 6) was paired with the primer 5'-TCCGCCTCGAACAGCCGCAGC-3' (SEQ ID NO: 7). The complete sequence of the Hm2-cDNA has been included (SEQ ID NO: 1). A predicted protein sequence is shown in SEQ ID NO: 2. The polypeptide encoded by this cDNA will function to degrade cyclic tetrapeptide toxins, and therefore confer disease resistance and/or act as a selectable marker gene in transformed plants.

All publication and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. An isolated polypeptide capable of conferring disease resistance in a plant to at least one pathogen comprising a polypeptide encoded by a polynucleotide having at least 90% identity to SEQ ID NO: 1.

2. The polypeptide of claim 1, wherein the polynucleotide comprises SEQ ID NO: 1.

3. The polypeptide of claim 1 wherein the pathogen is *C. carbonum*.

4. An isolated polypeptide capable of conferring disease resistance in a plant to at least one pathogen comprising a polypeptide having at least 90% identity to SEQ ID NO: 2.

5. The polypeptide of claim 2 wherein We pathogen is *C. carbonum*.

6. An isolated polypeptide comprising SEQ ID NO: 2.

7. An isolated polypeptide capable of inactivating a cyclic tetrapeptide toxin comprising a polypeptide encoded by a polynucleotide having at least 90% identity to SEQ ID NO: 1.

8. The polypeptide of claim 7, wherein the polypeptide comprises a polypeptide encoded by a polynucleotide comprising the nucleic acid sequence of SEQ ID NO: 1.

9. An isolated polypeptide capable of inactivating a cyclic tetrapeptide toxin comprising a polypeptide having at least 90% identity to SEQ ID NO: 2.

10. The polypeptide of claim 9, wherein the polypeptide comprises an amino acid sequence of SEQ ID NO: 2.

11. The polypeptide of claim 7, wherein the cyclic tetrapeptide toxin is HC toxin.

12. The polypeptide of claim 8, wherein the cyclic tetrapeptide toxin is HC toxin.

13. The polypeptide of claim 9, wherein the cyclic tetrapeptide toxin is HC toxin.

14. The polypeptide of claim 10, wherein the cyclic tetrapeptide toxin is HC toxin.

* * * * *

UNITED STATES PATENT AND TRADEMARK OFFICE
CERTIFICATE OF CORRECTION

PATENT NO. : 6,486,302 B1
DATED : November 26, 2002
INVENTOR(S) : Steven P. Briggs et al.

It is certified that error appears in the above-identified patent and that said Letters Patent is hereby corrected as shown below:

<u>Title page</u>,
Item [73], Assignee, should read as follows:
-- [73]   Assignee:   Pioneer Hi-Bred International, Inc.
                     Des Moines, IA (US)

The Curators of the University of Missouri
                     Columbia, MO (US) --

Signed and Sealed this

Eighth Day of June, 2004

JON W. DUDAS
*Acting Director of the United States Patent and Trademark Office*